US009314368B2

(12) United States Patent
Allison et al.

(10) Patent No.: US 9,314,368 B2
(45) Date of Patent: Apr. 19, 2016

(54) HOME-USE APPLICATORS FOR NON-INVASIVELY REMOVING HEAT FROM SUBCUTANEOUS LIPID-RICH CELLS VIA PHASE CHANGE COOLANTS, AND ASSOCIATES DEVICES, SYSTEMS AND METHODS

(75) Inventors: John W. Allison, Los Altos, CA (US); Mitchell E. Levinson, Pleasanton, CA (US); Jesse N. Rosen, Albany, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 491 days.

(21) Appl. No.: 13/013,579

(22) Filed: Jan. 25, 2011

(65) Prior Publication Data

US 2011/0238050 A1 Sep. 29, 2011

Related U.S. Application Data

(60) Provisional application No. 61/298,175, filed on Jan. 25, 2010, provisional application No. 61/354,615, filed on Jun. 14, 2010.

(51) Int. Cl.
*A61B 18/02* (2006.01)
*A61F 7/02* (2006.01)
*A61F 7/00* (2006.01)

(52) U.S. Cl.
CPC .......... *A61F 7/02* (2013.01); *A61F 2007/0056* (2013.01); *A61F 2007/0096* (2013.01); *A61F 2007/029* (2013.01); *A61F 2007/0292* (2013.01)

(58) Field of Classification Search
CPC ................................................. A61F 2007/029
USPC ................... 607/96, 104; 165/46; 606/22
See application file for complete search history.

(56) References Cited

U.S. PATENT DOCUMENTS 681,806 A 9/1901 Mignault
889,810 A 6/1908 Robinson
(Continued)

FOREIGN PATENT DOCUMENTS

AU 2011253768 6/2012
CA 2441489 3/2005
(Continued)

OTHER PUBLICATIONS

Ardevol, "Cooling rates of tissue samples during freezing with liquid nitrogen," J. of Biochem and Biophysical Methods, 27, 77-86 (1993).
(Continued)

*Primary Examiner* — Michael Peffley
*Assistant Examiner* — Thomas Giuliani
(74) *Attorney, Agent, or Firm* — Perkins Coie LLP

(57) ABSTRACT

Home-use applicators for non-invasively removing heat from subcutaneous, lipid-rich cells via phase change coolants, and associated devices, systems and methods. A device in accordance with a particular embodiment includes an applicator releasably positionable in thermal communication with human skin, and a coolant vessel having a coolant. The device further includes a heat transfer conduit operatively coupled to the applicator and housing a heat transfer fluid that is isolated from fluid contact with the coolant. A heat exchanger is operatively coupled between the coolant vessel and the heat transfer conduit to transfer heat between the heat transfer fluid and the coolant, and a fluid driver is operatively coupled to the heat transfer conduit to direct the heat transfer fluid between the applicator and the heat exchanger.

20 Claims, 10 Drawing Sheets

(56) References Cited

U.S. PATENT DOCUMENTS

| | | |
|---|---|---|
| 2,516,491 A | 7/1950 | Swastek |
| 2,726,658 A | 12/1955 | Chessey |
| 2,766,619 A | 10/1956 | Tribus et al. |
| 2,851,602 A | 9/1958 | Cramwinckel et al. |
| 3,093,135 A | 6/1963 | Hirschhorn |
| 3,132,688 A | 5/1964 | Nowak |
| 3,282,267 A | 11/1966 | Wiliam |
| 3,502,080 A | 3/1970 | Hirschhorn |
| 3,587,577 A | 6/1971 | Smirnov et al. |
| 3,591,645 A | 7/1971 | Selwitz |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,026,299 A | 5/1977 | Sauder |
| 4,140,130 A | 2/1979 | Storm, III |
| 4,149,529 A | 4/1979 | Copeland et al. |
| 4,178,429 A | 12/1979 | Scheffer |
| 4,202,336 A | 5/1980 | van Gerven et al. |
| 4,266,043 A | 5/1981 | Fujii et al. |
| 4,269,068 A | 5/1981 | Molina |
| 4,381,009 A | 4/1983 | Del Bon et al. |
| 4,396,011 A | 8/1983 | Mack et al. |
| 4,459,854 A | 7/1984 | Richardson et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt et al. |
| 4,741,338 A | 5/1988 | Miyamae et al. |
| 4,764,463 A | 8/1988 | Mason et al. |
| 4,802,475 A | 2/1989 | Weshahy et al. |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A * | 10/1990 | Golden .................. 607/104 |
| 4,990,144 A | 2/1991 | Blott |
| 5,007,433 A | 4/1991 | Hermsdorffer et al. |
| 5,018,521 A | 5/1991 | Campbell |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen et al. |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney |
| 5,327,886 A | 7/1994 | Chiu |
| 5,330,745 A | 7/1994 | McDow |
| 5,333,460 A * | 8/1994 | Lewis et al. .................. 62/6 |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan |
| 5,433,717 A | 7/1995 | Rubinsky et al. |
| 5,456,703 A | 10/1995 | Beeuwkes, III |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards |
| 5,507,790 A | 4/1996 | Weiss et al. |
| 5,514,105 A | 5/1996 | Goodman, Jr. et al. |
| 5,514,170 A | 5/1996 | Mauch |
| 5,531,742 A | 7/1996 | Barken |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal et al. |
| 5,628,769 A | 5/1997 | Saringer et al. |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay |
| 5,660,836 A | 8/1997 | Knowlton |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,736 A | 5/1998 | Tankovich |
| 5,755,663 A | 5/1998 | Larsen et al. |
| 5,755,753 A | 5/1998 | Knowlton |
| 5,755,755 A | 5/1998 | Panyard |
| 5,759,182 A | 6/1998 | Varney et al. |
| 5,759,764 A | 6/1998 | Polovina |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,814,040 A | 9/1998 | Nelson et al. |
| 5,817,050 A | 10/1998 | Klein |
| 5,817,149 A | 10/1998 | Owens et al. |
| 5,817,150 A | 10/1998 | Owens et al. |
| 5,830,208 A | 11/1998 | Muller |
| 5,833,685 A | 11/1998 | Tortal et al. |
| 5,844,013 A | 12/1998 | Kenndoff et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer et al. |
| 5,901,707 A | 5/1999 | Gon.cedilla.alves et al. |
| 5,902,256 A | 5/1999 | Benaron |
| 5,919,219 A | 7/1999 | Knowlton |
| 5,944,748 A | 8/1999 | Mager et al. |
| 5,948,011 A | 9/1999 | Knowlton |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |

(56) References Cited

U.S. PATENT DOCUMENTS

| | | |
|---|---|---|
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao |
| 6,071,239 A | 6/2000 | Cribbs et al. |
| 6,074,415 A | 6/2000 | Der Ovanesian |
| 6,093,230 A | 7/2000 | Johnson, III et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chomenky et al. |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee et al. |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |

(56) References Cited

U.S. PATENT DOCUMENTS

| | | |
|---|---|---|
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,834,547 B2 | 9/2014 | Anderson et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1* | 11/2001 | Elkins et al. ............... 607/104 |
| 2001/0045104 A1 | 11/2001 | Bailey et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0069618 A1 | 4/2003 | Smith et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1* | 7/2005 | Noel ....................... 165/104.21 |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1* | 11/2005 | Anderson et al. ............... 606/20 |
| 2005/0261753 A1 | 11/2005 | Littrup et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0122509 A1 | 6/2006 | Desilets |

(56) References Cited

U.S. PATENT DOCUMENTS

| | | |
|---|---|---|
| 2006/0189964 A1 | 8/2006 | Anderson et al. |
| 2006/0200063 A1 | 9/2006 | Munro et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0312651 A1 | 12/2008 | Pope et al. |
| 2009/0012434 A1 | 1/2009 | Anderson |
| 2009/0018623 A1* | 1/2009 | Levinson et al. ............... 607/96 |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0276018 A1 | 11/2009 | Brader |
| 2009/0281464 A1 | 11/2009 | Cioanta et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1* | 12/2009 | El-Galley ..................... 607/105 |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Michael |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158636 A1 | 6/2013 | Ting et al. |
| 2013/0166003 A1 | 6/2013 | Johnson et al. |
| 2013/0185440 A1 | 7/2013 | Blau et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |

(56) References Cited

U.S. PATENT DOCUMENTS

| | | | |
|---|---|---|---|
| 2014/0142469 | A1 | 5/2014 | Britva et al. |
| 2014/0200488 | A1 | 7/2014 | Seo et al. |
| 2014/0277302 | A1 | 9/2014 | Weber et al. |
| 2015/0216719 | A1 | 8/2015 | DeBenedictis et al. |
| 2015/0216720 | A1 | 8/2015 | DeBenedictis et al. |
| 2015/0216816 | A1 | 8/2015 | O'Neil et al. |

FOREIGN PATENT DOCUMENTS

| | | | |
|---|---|---|---|
| CH | 333982 | A | 11/1958 |
| CN | 86200604 | U | 10/1987 |
| CN | 2514795 | Y | 10/2002 |
| CN | 1511503 | | 7/2004 |
| CN | 1741777 | | 3/2006 |
| CN | 1817990 | | 8/2006 |
| CN | 2843367 | Y | 12/2006 |
| CN | 2850584 | Y | 12/2006 |
| CN | 2850585 | Y | 12/2006 |
| CN | 200970265 | Y | 11/2007 |
| DE | 4213584 | | 11/1992 |
| DE | 4224595 | | 1/1994 |
| DE | 4238291 | A1 | 5/1994 |
| DE | 4445627 | A1 | 6/1996 |
| DE | 19800416 | A1 | 7/1999 |
| EP | 0263069 | | 4/1988 |
| EP | 0397043 | | 11/1990 |
| EP | 0406244 | | 1/1991 |
| EP | 0598824 | | 6/1994 |
| EP | 1030611 | A1 | 8/2000 |
| EP | 1568395 | A1 | 8/2005 |
| EP | 2260801 | A2 | 12/2010 |
| EP | 2289598 | A1 | 3/2011 |
| EP | 2527005 | A1 | 11/2012 |
| FR | 854937 | A | 4/1940 |
| FR | 2744358 | A1 | 8/1997 |
| FR | 2767476 | A1 | 2/1999 |
| FR | 2776920 | A1 | 10/1999 |
| FR | 2789893 | A1 | 8/2000 |
| FR | 2805989 | A1 | 9/2001 |
| GB | 387960 | A | 2/1933 |
| GB | 2120944 | A | 12/1983 |
| GB | 2248183 | A | 4/1992 |
| GB | 2263872 | A | 8/1993 |
| GB | 2286660 | | 8/1995 |
| GB | 2323659 | | 9/1998 |
| JP | 63076895 | | 4/1988 |
| JP | 01223961 | A | 9/1989 |
| JP | 03051964 | | 3/1991 |
| JP | 3259975 | | 11/1991 |
| JP | 4093597 | | 3/1992 |
| JP | 6282977 | | 10/1994 |
| JP | 7194666 | | 8/1995 |
| JP | 7268274 | | 10/1995 |
| JP | 09164163 | | 6/1997 |
| JP | 10216169 | | 8/1998 |
| JP | 2000503154 | | 3/2000 |
| JP | 3065657 | | 7/2000 |
| JP | 2001046416 | | 2/2001 |
| JP | 2001046416 | A | 2/2001 |
| JP | 2002543668 | | 12/2002 |
| JP | 2004013600 | | 1/2004 |
| JP | 2004159666 | A | 6/2004 |
| JP | 2005039790 | | 2/2005 |
| JP | 3655820 | | 3/2005 |
| JP | 200565984 | | 3/2005 |
| JP | 2005110755 | | 4/2005 |
| JP | 2005520608 | | 7/2005 |
| JP | 2005237908 | A | 9/2005 |
| JP | 2006026001 | | 2/2006 |
| JP | 2006130055 | A | 5/2006 |
| JP | 2006520949 | | 9/2006 |
| JP | 2008532591 | | 8/2008 |
| JP | 2009189757 | | 8/2009 |
| JP | 2009189757 | A | 8/2009 |
| KR | 200173222 | Y1 | 12/1999 |
| KR | 102004009450 | | 11/2004 |
| KR | 20090000258 | U | 1/2009 |
| KR | 1020130043299 | A | 4/2013 |
| KR | 1020140038165 | A | 3/2014 |
| RU | 2036667 | C1 | 6/1995 |
| SU | 532976 | | 11/1978 |
| TW | 0476644 | | 2/2002 |
| WO | WO-8503216 | | 8/1985 |
| WO | 9114417 | A1 | 10/1991 |
| WO | WO-94/04116 | | 3/1994 |
| WO | 9623447 | A1 | 8/1996 |
| WO | 9626693 | A1 | 9/1996 |
| WO | WO-96/36293 | | 11/1996 |
| WO | WO-96/37158 | | 11/1996 |
| WO | 9704832 | A1 | 2/1997 |
| WO | WO-97/05828 | | 2/1997 |
| WO | WO-9722262 | | 6/1997 |
| WO | 9724088 | A1 | 7/1997 |
| WO | WO-9725798 | | 7/1997 |
| WO | 9748440 | A1 | 12/1997 |
| WO | 9829134 | A2 | 7/1998 |
| WO | 9831321 | A1 | 7/1998 |
| WO | WO-98/41157 | | 9/1998 |
| WO | WO-9841156 | | 9/1998 |
| WO | 9909928 | A1 | 3/1999 |
| WO | 9916502 | A1 | 4/1999 |
| WO | WO-9938469 | | 8/1999 |
| WO | 9944552 | A1 | 9/1999 |
| WO | 9949937 | A1 | 10/1999 |
| WO | WO-00/44346 | | 8/2000 |
| WO | WO-00/65770 | | 11/2000 |
| WO | WO-0067685 | | 11/2000 |
| WO | 0100269 | A1 | 1/2001 |
| WO | 0113989 | | 3/2001 |
| WO | WO-0114012 | | 3/2001 |
| WO | 0134048 | A1 | 5/2001 |
| WO | WO-0205736 | | 1/2002 |
| WO | WO-02/102921 | | 12/2002 |
| WO | WO-03078596 | | 9/2003 |
| WO | 03079916 | A1 | 10/2003 |
| WO | WO-04/000098 | | 12/2003 |
| WO | WO-2004080279 | | 9/2004 |
| WO | WO-2005033957 | | 4/2005 |
| WO | WO-2005046540 | | 5/2005 |
| WO | 2005060354 | A2 | 7/2005 |
| WO | 2005112815 | A1 | 12/2005 |
| WO | WO-2006066226 | | 6/2006 |
| WO | WO-2006094348 | | 9/2006 |
| WO | WO-2006106836 | | 10/2006 |
| WO | 2006116603 | A2 | 11/2006 |
| WO | WO-2006127467 | | 11/2006 |
| WO | WO-2007012083 | | 1/2007 |
| WO | 2007028975 | A1 | 3/2007 |
| WO | WO-2007041642 | | 4/2007 |
| WO | WO-2007127924 | | 11/2007 |
| WO | 2007145421 | A1 | 12/2007 |
| WO | 2007145422 | A1 | 12/2007 |
| WO | 2008006018 | A2 | 1/2008 |
| WO | 2008039556 | A1 | 4/2008 |
| WO | WO-2008039557 | | 4/2008 |
| WO | 2008055243 | A2 | 5/2008 |
| WO | WO-2008143678 | | 11/2008 |
| WO | WO-2009/011708 | | 1/2009 |
| WO | WO-2009026471 | | 2/2009 |
| WO | WO-2010077841 | | 7/2010 |
| WO | WO-2010127315 | | 11/2010 |
| WO | WO-2012012296 | | 1/2012 |
| WO | WO-2012103242 | | 8/2012 |
| WO | 2013013059 | A1 | 1/2013 |
| WO | 2013075006 | A1 | 5/2013 |
| WO | 2013075016 | A1 | 5/2013 |
| WO | 2013190337 | A1 | 12/2013 |
| WO | 2014151872 | A3 | 9/2014 |
| WO | 2015117001 | A1 | 8/2015 |
| WO | 2015117026 | A2 | 8/2015 |

(56) References Cited

FOREIGN PATENT DOCUMENTS

WO    2015117032 A1    8/2015
WO    2015117036 A2    8/2015

OTHER PUBLICATIONS

Bohm et al., "Saline-enhanced radiofrequency ablation of breast tissue: an in vitro feasibility study," Invest Radiol, 2000, pp. 149-57, vol. 35—issue (3).
Bondei, E. et al., "Disorders of Subcutaneous Tissue (Cold Panniculitis)," Dermatology in General Medicine, Chapter 108, Section 16: 1333-1334, 1993.
Burge, S.M. et al., "Hair Follicle Destruction and Regeneration in Guinea Pig Skin after Cutaneous Freeze Injury," Cryobiology, 27(2): 153-163, 1990.
Coban, "Ischemia-Reperfusion Injury of Adipofascial Tissue: An Experimental Study Evaluating early Histologic and Biochemical Alterations in Rats," Mediators of Inflammation, 2005, 5, 304-308.
Donski et al., "The Effects of Cooling no Experimental Free Flap Survival," Brit J Plas Surg, 1980, pp. 353-360, vol. 33.
Duncan, W.C. et al., "Cold Panniculitis," Arch. Derm., 94:722-24, 1966.
Epstein, E.H. et al., "Popsicle Panniculitis," The New England Journal of Medicine, 282(17):996-67, 1970.
European Search Report, European Application No. EP07758558.6; Applicant: Zeltiq Aesthetics, Inc.; Mailed on Jul. 20, 2007, 4 pages.
European Search Report, European Patent Application No. 10167756.5, Applicant: The General Hospital Corporation, Mailing Date: Aug. 31, 2010, 6 pages.
European Search Report, Eurpean Patent Application No. EP07761461; Applicant: Zeltiq Aesthetics, Inc., Mailing Date: Apr. 25, 2012, 9 pages.
European Search Report, Supplement, European Patent Application No. EP08798416.7, Applicant: Zeltiq Aesthetics, Inc., Mailing Date: Jan. 12, 2012, 7 pages.
European Search Report, Supplement, European Patent Application No. EP09836823, Applicant: Zeltiq Aesthetics, Inc., Mailing Date: May 15, 2012, 5 pages.
Final Office Action; U.S. Appl. No. 10/391,221; Date of Mailing: Aug. 24, 2006, 4 pages.
Final Office Action; U.S. Appl. No. 11/016,196; Date of Mailing: Mar. 23, 2010, 12 pages.
Final Office Action; U.S. Appl. No. 11/435,502; Date of Mailing: Mar. 29, 2010, 11 pages.
Final Office Action; U.S. Appl. No. 11/528,225; Date of Mailing: Dec. 29, 2010, 9 pages.
Final Office Action; U.S. Appl. No. 11/558,046; Date of Mailing: Mar. 30, 2011, 17 pages.
Final Office Action; U.S. Appl. No. 11/741,271; Date of Mailing: Jul. 19, 2012, 8 pages.
Final Office Action; U.S. Appl. No. 11/750,953; Date of Mailing: Jul. 5, 2012, 11 pages.
Gage, "Current Progress in Cryosurgery," Cryobiology 25, 483-486 (1988).
Hale et al., "Influence of chronic heat exposure and prolonged food deprivation on execretion of magnesium, phosphorus, calcium, hydrogen ion & ketones," Aerosp Med, 1968, pp. 919-926, vol. 39—issue (9).
Heller-Page et al., "Temperature-dependent skin disorders," Journal of the American Academy of Dermatology, May 1988, vol. 18, No. 5, Pt 1, pp. 1003-1019.
Hemmingsson, "Attenuation in Human muscle and Fat Tissue in Vivo and in Vitro," Acta Radiologica Diagnosis 23, 149-151 (1982).
Henry et al.,"Les Dermatoses Hivernales," Rev Med Liege, 1999, 54:11, 864-866. [Abstract Attached].
Holman, "Variation in cryolesion penetration due to probe size and tissue thermal conductivity," Ann. Thorac. Surg. 53, 123-126 (1992).
Hong, "Patterns of Ice Formulation in Normal and Malignant Breast Tissue," Cryobiology 31, 109-120 (1994).

International Search Report and Written Opinion for PCT/US2005/045988; Applicant: The General Hospital Corporation; Mailed on Apr. 25, 2006, 14 pages.
International Search Report and Written Opinion for PCT/US2007/023492; Applicant: Zeltiq Aesthetics, Inc.; Date of Mailing: May 15, 2008, 7 pages.
International Search Report and Written Opinion for PCT/US2007/062508; Applicant: Juniper Medical, Inc.; Date of Mailing: Jul. 20, 2007, 13 pages.
International Search Report and Written Opinion for PCT/US2007/064016; Applicant: Juniper Medical, Inc.; Date of Mailing: Jul. 20, 2007, 13 pages.
International Search Report and Written Opinion for PCT/US2007/064017; Applicant: Juniper Medical, Inc.; Date of Mailing: Oct. 26, 2007, 16 pages.
International Search Report and Written Opinion for PCT/US2007/064018; Applicant: Juniper Medical, Inc.; Date of Mailing: Jul. 26, 2007, 13 pages.
International Search Report and Written Opinion for PCT/US2007/067638; Applicant: Juniper Medical, Inc.; Date of Mailing: Jan. 10, 2008, 11 pages.
International Search Report and Written Opinion for PCT/US2007/069694; Applicant: Juniper Medical, Inc.; Date of Mailing: Nov. 23, 2007, 12 pages.
International Search Report and Written Opinion for PCT/US2007/075935; Applicant: Zeltiq Aesthetics, Inc.; Date of Mailing: Apr. 10, 2008, 12 pages.
International Search Report and Written Opinion for PCT/US2007/083255; Applicant: Zeltiq Aesthetics, Inc.; Date of Mailing: Aug. 11, 2008, 8 pages.
International Search Report and Written Opinion for PCT/US2008/073930; Applicant: Zeltiq Aesthetics, Inc.; Date of Mailing: Nov. 7, 2008, 10 pages.
International Search Report and Written Opinion for PCT/US2009/058088; Applicant: Zeltiq Aesthetics, Inc.; Date of Mailing: Nov. 20, 2009, 14 pages.
International Search Report and Written Opinion for PCT/US2009/067973; Applicant: Zeltiq Aesthetics, Inc.; Date of Mailing: Feb. 18, 2010, 10 pages.
International Search Report and Written Opinion for PCT/US2010/033290; Applicant: Zeltiq Aesthetics, Inc.; Mailed on Feb. 25, 2011, 12 pages.
International Search Report and Written Opinion for PCT/US2011/022112; Applicant: Zeltiq Aesthetics, Inc.; Mailed on Mar. 18, 2011, 11 pages.
International Search Report and Written Opinion for PCT/US2011/022444; Applicant: Zeltiq Aesthetics, Inc., Mailed on Mar. 29, 2011, 14 pages.
International Search Report and Written Opinion for PCT/US2012/022585; Mailed on May 18, 2012, 14 pages.
Kellum, R.E. et al., "Sclerema Neonatorum: Report of Case and Analysis of Subcutaneous and Epidermal-Dermal Lipids by Chromatographic Methods," *Arch. Derm.*, 97:372-80, 1968.
Koska, J. et al., "Endocrine Regulation of Subcutaneous Fat Metabolism During Cold Exposure in Humans," Ann N.Y. Acad, Sci., 967:500-05, 2002.
Kundu et al., "Breath acetone analyzer: diagnostic tool to monitor dietary fat loss," Clin Chem, 1993, pp. 87-92, vol. 39, issue (1).
Kundu et al., "Novel solid-phase assay of ketone bodies in urine," Clin Chem, 1991, pp. 1565-1569, vol. 37—issue (9).
Kuroda et al., "Thermal distribution of radio-frequency inductive hyperthermia using an inductive aperture-type applicator: evaluation of the effect of tumour size and depth," Med Biol Eng Comput, 1999, pp. 285-290, vol. 37—issue (3).
Laugier, et al., "In Vivo Results with a New Device for Ultrasonic Monitoring of Pig Skin Cryosurgery: The Echographic Cryoprobe," The society for Investigative Dermatology, Inc., vol. 111(2), Aug. 1998.
Levchenko, et al., "Effect of dehydration on lipid metabolism," WMJ, 1978, pp. 95-97, vol. 50—issue (1).
Lidagoster, MD et al., "Comparison of Autologous Fat Transfer in Fresh, Refrigerated, and Frozen Specimens: An Animal Model Pre-

(56) References Cited

OTHER PUBLICATIONS sented," at the 16th Annual Meeting of the Northeastern Society of Plastic Surgeons: Burlington, VT, 1999, pp. 512-515.
Liu, A.Y.C. et al., "Transient Cold Shock Induces the Heat Shock Response upon Recovery at 37 C in Human Cells," J. Biol. Chem., May 20, 1994, 269(20), 14768-14775.
Lvova, "Lipid levels and lipid peroxidation in frog tissues during hypothermia and hibernation," WMJ, 1990, pp. 65-70, vol. 62—issue (1).
Maize, J.C., "Panniculitis," Cutaneous Pathology, Chapter 13:327-344, 1998.
Malcolm, G. et al., "Fatty Acid Composition of Adipose Tissue in Humans: Differences between Subcutaneous Sites," Am J Clin. Nutr., 50(2):288-91, 1989.
Merrill, Tom, "A Chill to the Heart: A System to Deliver Local Hypothermia Could One Day Improve the Lives of Heart-Attack Patients," Mechanical Engineering Magazine, Oct. 2010 (10 pages).
Moschella, S.L. et al., "Diseases of the Subcutaneous Tissue," Derm., Section 2:1169-1181, 1985.
Murphy, J.V. et al., "Frostbite: Pathogenesis and Treatment," The Journal of Trauma: Injury, Infection, and Critical Care, 48(1):171-178, 2000.
Nagao et al., "Dietary diacylglycerol suppresses accumulation of body fat compared to triacylglycerol in men a double-blind controlled trial," J Nutr, 2000, pp. 792-797, vol. 130—issue (4).
Nagore et al., "Lipoatrophia semicircularis-a traumatic panniculitis: Report of seven cases and review of the literature," Journal of the American Academy of Dermatology, Nov. 1998, 39:879-81.
Nielsen, "Thermoregulation in Rest and Exercise," Acta Phys Scan Supp, 1969, pp. 6-74, vol. 323.
Nishikawa, "Ultrastructural Changes and Lipid Peroxidation in Rat Adipomusculocutaneous Flap Isotransplants after Normothermic Storage and Reperfusion," Transplantation, 1992, 54, 795-801.
Non-Final Office Action; U.S. Appl. No. 10/391,221; Date of Mailing: Jan. 25, 2006, 6 pages.
Non-Final Office Action; U.S. Appl. No. 10/391,221; Date of Mailing: May 30, 2007, 8 pages.
Non-Final Office Action; U.S. Appl. No. 10/391,221; Date of Mailing: Jul. 22, 2005, 6 pages.
Non-Final Office Action; U.S. Appl. No. 11/016,196; Date of Mailing: Apr. 22, 2008, 11 pages.
Non-Final Office Action; U.S. Appl. No. 11/016,196; Date of Mailing: Sep. 25, 2009, 8 pages.
Non-Final Office Action; U.S. Appl. No. 11/359,092; Date of Mailing: Nov. 19, 2009, 13 pages.
Non-Final Office Action; U.S. Appl. No. 11/435,502; Date of Mailing: Jul. 17, 2009, 10 pages.
Non-Final Office Action; U.S. Appl. No. 11/528,189; Date of Mailing Apr. 6, 2012, 9 pages.
Non-Final Office Action; U.S. Appl. No. 11/528,225; Date of Mailing: Apr. 12, 2010, 11 pages.
Non-Final Office Action; U.S. Appl. No. 11/528,225; Date of Mailing: Aug. 3, 2011, 11 pages.
Non-Final Office Action; U.S. Appl. No. 11/558,046; Date of Mailing: Jul. 12, 2010, 14 pages.
Non-Final Office Action; U.S. Appl. No. 11/741,271; Date of Mailing: Jul. 12, 2010, 9 pages.
Non-Final Office Action; U.S. Appl. No. 11/777,992; Date of Mailing: Jun. 22, 2012, 5 pages.
Non-Final Office Action; U.S. Appl. No. 12/337,544; Date of Mailing: Mar. 30, 2012, 13 pgs.
Non-Final Office Action; U.S. Appl. No. 12/565,613; Date of Mailing: Sep. 23, 2011, 32 pages.
Non-Final Office Action; U.S. Appl. No. 12/942,852; Date of Mailing: Mar. 7, 2011, 6 pages.
Non-Final Office Action; U.S. Appl. No. 12/942,852; Date of Mailing: Jun. 30, 2011, 10 pages.
Pease, "An Integrated Probe for Magnetic Resonance Imaging Monitored Skin Cryosurgery," Journal of Biomedical Engineering 117, 59-63, (1995).
Pech, "Attenuation values, volume changes and artifacts in tissue due to freezing," Acta Radiologica 6, 779-782 (1987).
Peterson et al., "Bilateral Fat Necrosis of the Scrotum, Urology Service, Department of Surgery, Dermatology Service, Department of Medicine and Department of Pediatrics," Letterman Army Medical Center, Journal of Urology, 1976, pp. 825-826, vol. 116, The Williams & Wilkins Co.
Phinney, S.D. et al., "Human Subcutaneous Adipose Tissue Shows Site-Specific Differences in Fatty Acid Composition," Am J. Clin. Nutr., 60:725-29, 1994.
Pre-Interview Office Action; U.S. Appl. No. 11/434,478; Date of Mailing: May 6, 2010, 4 pages.
Rabi, "Metabolic adaptations in brown adipose tissue of the hamster in extreme ambient temperatures," American Journal of Physiology 231, 153-160 (1976).
Renold, A.E., "Adipose Tissue," Handbook of Physiology, Chapter 15:170-76, 1965.
Rubinsky, "Cryosurgery: advances in the application of low temperatures to medicine," Int. J. Refrig. 190-199 (1991).
Schoning, et al., "Experimental Frostbite: Freezing Times, Rewarming Times, and Lowest Temperatures of Pig Skin Exposed to Chilled Air," Cryobiology, 1990, pp. 189-193, 27.
Shephard, "Adaptation to Exercise in the Cold," Sports Medicine, 1985, 2.59-71.
Wang et al., "Cryopreservation of cell/hydrogel constructs based on a new cell-assembling technique", Sep. 5, 2009, 40 pages.
Wharton et al., "Cold acclimation and cryoprotectants in a freeze-tolerant Antarctic nematode, Panagrolaimus davidi," Mar. 7, 2000, 2 pages.
Winkler et al., "Gene Transfer in Laboratory Fish: Model Organisms for the Analysis of Gene Function," Transgenic Animals, 1997, pp. 387-395.
Young, H.E. et al., "Isolation of Embryonic Chick Myosatellite and Pluripotent Stem Cells," J. Tiss. Cult. Meth., 14:85-92, 1992.
U.S. Appl. No. 11/435,502, filed May 17, 2006, Levinson.
U.S. Appl. No. 11/528,189, filed Sep. 26, 2006, Levinson et al.
U.S. Appl. No. 11/528,225, filed Sep. 26, 2006, Levinson et al.
U.S. Appl. No. 11/741,271, filed Apr. 27, 2007, Levinson et al.
U.S. Appl. No. 11/750,953, filed May 18, 2007, Rosen et al.
U.S. Appl. No. 11/777,992, filed Jul. 13, 2007, Levinson et al.
U.S. Appl. No. 11/777,995, filed Jul. 13, 2007, Levinson et al.
U.S. Appl. No. 11/777,999, filed Jul. 13, 2007, Levinson et al.
U.S. Appl. No. 11/778,001, filed Jul. 13, 2007, Levinson et al.
U.S. Appl. No. 11/778,003, filed Jul. 13, 2007, Levinson et al.
U.S. Appl. No. 12/196,246, filed Jun. 11, 2009, Levinson.
U.S. Appl. No. 12/275,002, filed Nov. 20, 2008, Martens.
U.S. Appl. No. 12/275,014, filed Nov. 20, 2008, Martens.
U.S. Appl. No. 12/337,544, filed Jun. 17, 2010, Alison.
International Preliminary Examining Authority Written Opinion for PCT/US2007/67638; Application Levinson et al. Date of Mailing: Jun. 8, 2010.
International Preliminary Examining Authority Written Opinion for PCT/US2007/67638; Application Levinson et al. Date of Mailing: Sep. 21, 2010, 7 pages.
International Search Report and Written Opinion for PCT/US2011/044270; Applicant: Zeltiq Aesthetics, Inc.; Mailed on Nov. 21, 2011. 9 pages.
Office Action; Canadian Patent Application No. 2,585,136; Applicant Zeltiq Aesthetics, Inc.; Mailed on Nov. 13, 2008; 3 pages.
Office Action; Canadian Patent Application No. 2,585,192; Applicant Zeltiq Aesthetics, Inc.; Mailed on Nov. 13, 2008; 3 pages.
Office Action; Canadian Patent Application No. 2,585,214; Applicant Zeltiq Aesthetics, Inc.; Mailed on Nov. 13, 2008; 3 pages.
Pierard, G.E., Nizet, J.L., Pierard-Franchimont, C., "Cellulite: From Standing Fat Herniation to Hypodermal Stretch Marks," Am. J. Dermatol. 22:1, 34-37, 2000.
Pope, "Selective Firbous Septae Heating", Thermage Article, Feb. 2005, 7pgs.
PubMed, "Cold shock induces the synthesis of stress proteins in human kerantinocytes", Holland DB. Aug. 1993; 101(2): 196-9.
PubMed, "Effects of thermal shocks on interleukin-1 levels and heat shock protein 72 (HSP72) expression in normal human keratinocytes", Arch Dermatol Res. 1992; 284(7): 414-7.

(56) References Cited

OTHER PUBLICATIONS

Quinn, P.J., "A Lipid Phase Separation Model of Low Temperature Damage to Biological Membranes" Cryobiology, 22: 128-147, 1985.
Rossi, "Cellulite: a Review" 2000, 251-262, 12 pgs.
Rubinsky, B., "Principles of Low Temperature Preservation" Heart Failure Reviews, 8, 277-284 (2003).
Search Results report, Jun. 29, 2012, 2 pgs.
Sigma-Aldrich "Polyethylene glycol and Polyethylene oxide," http://www.sigmaaldrich.com/materials-science/materialscience-;products.htmi?TablePage=2020411 0, accessed Oct. 19, 2012.
Smalls, "Quantitative Model of Cellulite: Three Dimensional Skin Surgace Topography, Biophsical Characterization and Relationship to Human Perception", 17 pgs.
Thermage, News Release, "Study Published in Facial Plastic Surgery Journal Finds Selective Heating of Fibrous Septae Key to Success and Safety of Thermage ThermoCool System", Jun. 20, 2005, 2 pages.
Vallerand, A.L., Zamecnik. J., Jones, P.J.H. Jacobs, I. "Cold Stress Increases Lipolysis, FFA RA and TG/FFA Cycling in Humans" Aviation, Space, and Environmental Medicine 70, 42-50 (1999).
Alster, Tina et el. "Cellulite treatment using a novel combination radiofrequency, infrared light, and mechanical tissue manipulation device," J. of Cosmetic and Laser Therapy, vol. 7, 2005, p. 81-85.
Duck, Francis A., Physical Properties of Tissue, Academic Press Ltd., 1990, chapters 4 & 5, pp. 73-165.
Fournier, Luc et al. "Lattice model for the kinetics of rupture of fluid bilayer membranes," Physical Review, vol. 67, 2003, 051908-1-051908-11.
Gabriel, S. et al., "The dielectric properties of biological tissue: II. Measurements in the frequency range 10 Hz to 20 GHz," Phys. Medical Biology, vol. 41, 1996, p. 2251-2269.
Non-Final Office Action mailed Feb. 27, 2015; U.S. Appl. No. 13/013,603; 17 pages.
Isambert, Nerve "Understanding the Electroporation of Cells and Artificial Bilayer Membranes," Phys. Review Letters, vol. 80, 1998, pp. 3404-3707.
Saleh, K.Y. et el. "Two-dimensional ultrasound phased array design for tissue ablation for treatment of benign hyperplasia," Int. J. Hyperthermia, vol. 20, No. 1, Feb. 2004, p. 7-31.
Ardevol, et al., "Cooling Rates of Tissue Samples During Freezing with Liquid Nitrogen", Journal of Biochem and Biophysical Methods, 27, 1993, 77-86.
Peterson, et al., "Bilateral Fat Necrosis of the Scrotum", 116 Journal of Urology, 1976, 825-826.
Schoning, et al., "Experimental Frostbite: Freezing Times, Rewarming Times, and Lowest Temperatures of Pig Skin Exposed to Chilled Air", 27 Cryobiology, 1990, 189-193.
Aguilar et al., "Modeling Cryogenic Spray Temperature and Evaporation Rate Based on Single-Droplet Analysis", Eighth International Conference on Liquid Atomization and Spray Systems, Pasadena, CA, USA, Jul. 2000, 7 pages.
European Search Report; Application No. EP14156801.4; Dated Aug. 22, 2014; Applicant: Zeltiq Aesthetics, Inc. 5 pgs.
Final Office Action, U.S. Appl. No. 13/013,579, Date of Mailing: Jun. 20, 2014, 15 pages.
Final Office Action; U.S. Appl. No. 13/013,603; Date of Mailing Jul. 17, 2014, 17 pages.
International Search Report and Written Opinion for PCT/US2014/026558; Mailed on Oct. 24, 2014, 16 pages.
Zouboulis et al., "Current Developments and Users of Cryosurgery in the Treatment of Keloids and Herpertrophic Scars", Wound Repair and Regeneration, vol. 10, No. 2, pp. 98-102, 2002.
Manstein, D. et al., "Selective Cryolysis: A Novel Method of Non-Invasive Fat Removal", 40 Lasers in Surgery & Medicine, 2008, pp. 595-604.
Hernan, P. et al., "Study for the evaluation of the efficacy of Lipocryolysis (EEEL)", Nov. 30, 2011.
Hernan, P., "A Study to Evaluate the Action of Lipocryolysis", 33(3) CryoLellers, 2012, pp. 176-180.
Jalian, H. R. et al., "Cryolipolysis: A Historical Perspective and Current Clinical Practice", 32(1) Semin. Cutan. Med. Surg., 2013, pp. 31-34.
Zelickson, B. et al., "Cryolipolysis for Noninvasive Fat Cell Destruction: Initial Results from a Pig Model", 35 Dermatol. Sug., 2009, pp. 1-9.

* cited by examiner

HOME-USE APPLICATORS FOR NON-INVASIVELY REMOVING HEAT FROM SUBCUTANEOUS LIPID-RICH CELLS VIA PHASE CHANGE COOLANTS, AND ASSOCIATES DEVICES, SYSTEMS AND METHODS

CROSS-REFERENCE TO RELATED APPLICATIONS

The present application claims priority to the following U.S. Provisional Patent Applications, each of which is incorporated herein by reference: 61/298,175, filed Jan. 25, 2010 and 61/354,615, filed Jun. 14, 2010. To the extent that the materials in the foregoing references and/or any other references incorporated herein by reference conflict with the present disclosure, the present disclosure controls.

TECHNICAL FIELD

The present application relates generally to home-use applicators for non-invasively removing heat from subcutaneous lipid-rich cells via phase change coolants, and associated devices, systems and methods. In particular, several embodiments are directed to devices that a user may easily recharge or regenerate using a conventional commercial, clinical, institutional or domestic freezer.

BACKGROUND

Excess body fat, or adipose tissue, may be present in various locations of the body, including, for example, the thighs, buttocks, abdomen, knees, back, face, arms, chin, and other areas. Moreover, excess adipose tissue is thought to magnify the unattractive appearance of cellulite, which forms when subcutaneous fat protrudes into the dermis and creates dimples where the skin is attached to underlying structural fibrous strands. Cellulite and excessive amounts of adipose tissue are often considered to be unappealing. Moreover, significant health risks may be associated with higher amounts of excess body fat.

A variety of methods have been used to treat individuals having excess body fat and, in many instances, non-invasive removal of excess subcutaneous adipose tissue can eliminate unnecessary recovery time and discomfort associated with invasive procedures such as liposuction. Conventional non-invasive treatments for removing excess body fat typically include topical agents, weight-loss drugs, regular exercise, dieting or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or other negative reaction. Furthermore, fat loss in selective areas of a person's body often cannot be achieved using general or systemic weight-loss methods.

Other methods designed to reduce subcutaneous adipose tissue include laser-assisted liposuction and mesotherapy. Newer non-invasive methods include applying radiant energy to subcutaneous lipid-rich cells via, e.g., radio frequency and/or light energy, such as is described in U.S. Patent Publication No. 2006/0036300 and U.S. Pat. No. 5,143,063, or via, e.g., high intensity focused ultrasound (HIFU) radiation such as is described in U.S. Pat. Nos. 7,258,674 and 7,347,855. In contrast, methods and devices for non-invasively reducing subcutaneous adipose tissue by cooling are disclosed in U.S. Pat. No. 7,367,341 entitled "METHODS AND DEVICES FOR SELECTIVE DISRUPTION OF FATTY TISSUE BY CONTROLLED COOLING" to Anderson et al. and U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING" to Anderson et al., the entire disclosures of which are incorporated herein by reference.

BRIEF DESCRIPTION OF THE DRAWINGS

Many features of the present technology are illustrated in simplified, schematic and/or partially schematic formats in the following Figures to avoid obscuring significant technology features. Many features are not drawn to scale so as to more clearly illustrate these features.

DETAILED DESCRIPTION

1. Overview

Figure 1:
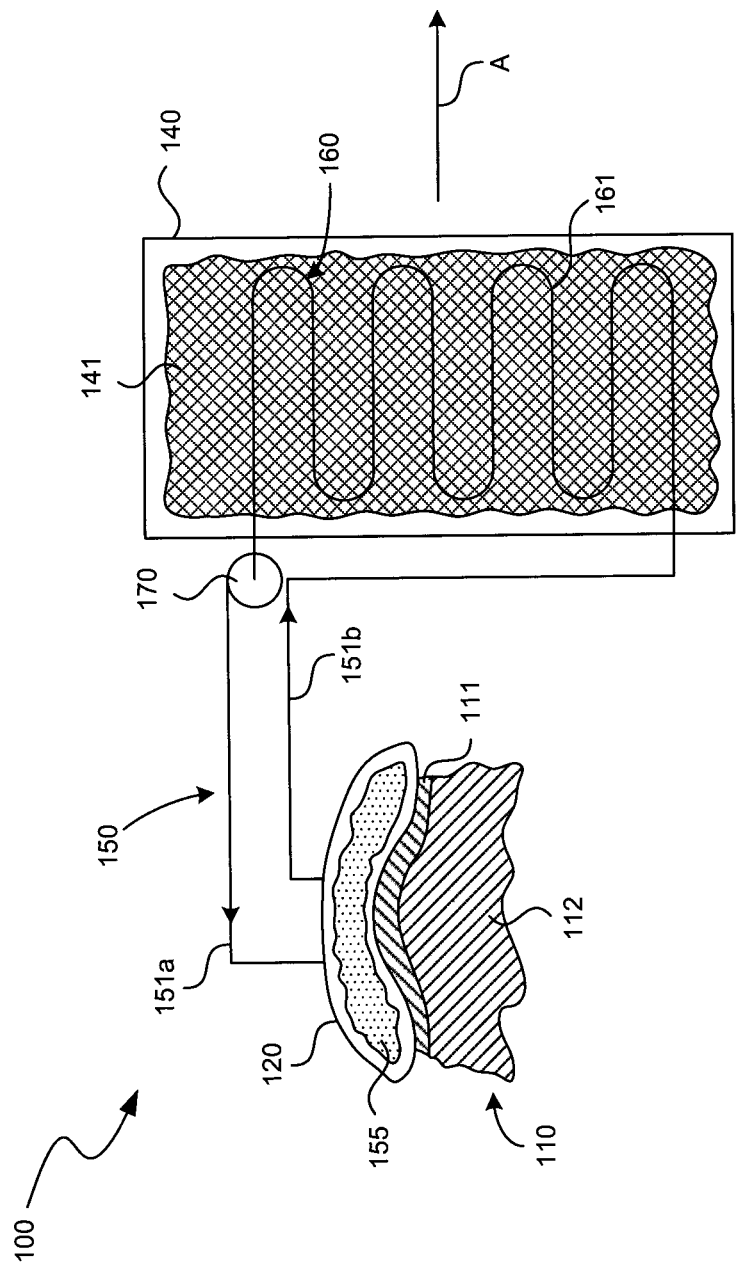
FIG. 1 is a partially schematic, partially cut-away illustration of a cooling device having a coolant vessel and heat exchanger configured in accordance with an embodiment of the disclosure.

Several examples of devices, systems and methods for cooling subcutaneous adipose tissue in accordance with the presently disclosed technology are described below. Although the following description provides many specific details of the following examples in a manner sufficient to enable a person skilled in the relevant art to practice, make and use them, several of the details and advantages described below may not be necessary to practice certain examples and methods of the technology. Additionally, the technology may include other examples and methods that are within the scope of the claims but are not described here in detail.

References throughout this specification to "one example," "an example," "one embodiment" or "an embodiment" mean that a particular feature, structure, or characteristic described in connection with the example is included in at least one example of the present technology. Thus, the occurrences of the phrases "in one example," "in an example," "one embodiment" or "an embodiment" in various places throughout this specification are not necessarily all referring to the same example. Furthermore, the particular features, structures, routines, steps or characteristics may be combined in any suitable manner in one or more examples of the technology. The headings provided herein are for convenience only and are not intended to limit or interpret the scope or meaning of the claimed technology.

Certain embodiments of the technology described below may take the form of computer-executable instructions, including routines executed by a programmable computer or controller. Those skilled in the relevant art will appreciate that the technology can be practiced on computer or controller systems other than those shown and described below. The technology can be embodied in a special-purpose computer, controller, or data processor that is specifically programmed, configured or constructed to perform one or more of the computer-executable instructions described below. Accordingly, the terms "computer" and "controller" as generally used herein refer to any data processor and can include internet appliances, hand-held devices, multi-processor systems, programmable consumer electronics, network computers, mini computers, and the like. The technology can also be practiced in distributed environments where tasks or modules are performed by remote processing devices that are linked through a communications network. Aspects of the technology described below may be stored or distributed on computer-readable media, including magnetic or optically readable or removable computer discs as well was media distributed electronically over networks. In particular embodiments, data structures and transmissions of data particular to aspects of the technology are also encompassed within the scope of the present technology. The present technology encompasses both methods of programming computer-readable media to perform particular steps, as well as executing the steps.

One embodiment of a cooling device for cooling subcutaneous lipid-rich cells in a human includes an applicator that is releasably positionable in thermal communication with human skin. The device further includes a coolant vessel having a coolant and a heat transfer conduit having a heat transfer fluid that is isolated from fluid contact with the coolant. A heat exchanger is operatively coupled between the coolant vessel and heat transfer conduit to transfer heat between the heat transfer fluid and the coolant, and a fluid driver is operatively coupled to the heat transfer conduit to direct the heat transfer fluid between the applicator and the heat exchanger.

In a further particular embodiment, the coolant has a liquid/solid phase transition temperature greater than the liquid/solid phase transition temperature of the heat transfer fluid. The heat exchanger is positioned within the coolant vessel and includes a heat exchanger conduit that, together with the heat transfer conduit and the applicator, form a sealed, closed-loop path for the heat transfer fluid. Accordingly, the entire device can be placed in a freezer (e.g., a domestic freezer) to freeze the coolant in preparation for treating lipid-rich cells in a human. In other embodiments, only selected components of the device are removable to freeze or otherwise cool the coolant.

A method for cooling human tissue in accordance with a particular embodiment of the disclosure includes releasably attaching an applicator to a human, and removing heat from subcutaneous lipid-rich tissue of the human via the applicator to selectively reduce lipid-rich cells of the tissue (e.g., via the body's reaction to cooling). The heat is removed by directing a chilled heat transfer fluid to applicator and transferring absorbed heat from the heat transfer fluid to a coolant. In particular embodiments, the coolant can remain solid, remain liquid or change phase from a solid to a liquid as it receives heat from the heat transfer fluid. The method still further includes re-cooling the coolant. Selected methods in accordance with another embodiment of the disclosure include removing the heat by directing a chilled heat transfer fluid into a flexible envelope and through a porous internal support structure within the envelope, while the porous internal structure at least restricts fluid pressure in the envelope from (a) bulging the envelope outwardly, or (b) collapsing the internal structure, or (c) both (a) and (b). Still another method includes directing the chilled heat transfer fluid into an applicator, between two flexible portions of the applicator, each having a different elasticity.

Without being bound by theory, the selective effect of cooling on lipid-rich cells is believed to result in, for example, membrane disruption, cell shrinkage, disabling, damaging, destroying, removing, killing or other methods of lipid-rich cell alteration. Such alteration is believed to stem from one or more mechanisms acting alone or in combination. It is thought that such mechanism(s) trigger an apoptotic cascade, which is believed to be the dominant form of lipid-rich cell death by non-invasive cooling. In any of these embodiments, the effect of tissue cooling is to selectively reduce lipid-rich cells.

Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation and chromosomal DNA fragmentation. Injury via an external stimulus, such as cold exposure, is one mechanism that can induce cellular apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" *Cryobiology* 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by macrophages. As a result, phagocytes can engulf and remove the dying cells (e.g., the lipid-rich cells) without eliciting an immune response. Temperatures that elicit these apoptotic events in lipid-rich cells may contribute to long-lasting and/or permanent reduction and reshaping of subcutaneous adipose tissue.

One mechanism of apoptotic lipid-rich cell death by cooling is believed to involve localized crystallization of lipids within the adipocytes at temperatures that do not induce crystallization in non-lipid-rich cells. The crystallized lipids selectively may injure these cells, inducing apoptosis (and may also induce necrotic death if the crystallized lipids damage or rupture the bi-lipid membrane of the adipocyte). Another mechanism of injury involves the lipid phase transition of those lipids within the cell's bi-lipid membrane, which results in membrane disruption or disfunction, thereby inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" *Heart Failure Reviews,* 8, 277-284 (2003). Another mechanism of injury may involve a disfunction of ion transfer pumps across the cellular membrane to maintain desired concentrations of ions such as potassium (K+) or sodium (Na+). An ion imbalance across the cell membrane may result from lipid phase transition of lipids within the cell's bi-lipid membrane or by another mechanism, thereby inducing apoptosis. Other yet-to-be-understood apoptotic mechanisms may exist, based on the relative sensitivity to cooling of lipid-rich cells compared to non-lipid rich cells.

In addition to the apoptotic mechanisms involved in lipid-rich cell death, local cold exposure is also believed to induce lipolysis (i.e., fat metabolism) of lipid-rich cells and has been shown to enhance existing lipolysis which serves to further increase the reduction in subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" *Aviation, Space and Environmental Medicine* 70, 42-50 (1999).

One expected advantage of the foregoing techniques is that the subcutaneous lipid-rich cells can be reduced generally without collateral damage to non-lipid-rich cells in the same region. In general, lipid-rich cells can be affected at low temperatures that do not affect non-lipid-rich cells. As a result, lipid-rich cells, such as those associated with cellulite, can be affected while other cells in the same region are generally not damaged even though the non-lipid-rich cells at the surface may be subjected to even lower temperatures than those to which the lipid-rich cells are exposed.

2. Representative Devices and Methods that Include Applicators, Coolant Vessels, and Heat Exchangers Arranged as a Single Unit FIG. 1 is a partially schematic, partially cut-away illustration of a device 100 having an applicator 120 operatively coupled to a coolant vessel 140 to cool human tissue 110. In particular, the device 100 is configured to cool a subcutaneous, lipid-rich tissue 112, without damaging the overlying dermis 111, generally in the manner described above. The applicator 120 is coupled to the coolant vessel 140 by a heat transfer conduit 150 that carries a heat transfer fluid 155. Accordingly, the heat transfer conduit 150 includes a supply portion 151a that directs the heat transfer fluid 155 to the applicator 120, and a return portion 151b that receives heat transfer fluid 155 exiting the applicator 120. The heat transfer fluid 155 is propelled through the heat transfer conduit 150 by a fluid driver 170, e.g., a pump or other suitable device. The heat transfer conduit 150 is typically insulated to prevent the ambient environment from heating the heat transfer fluid 155. Other elements of the device (aside from the cooling surface of the applicator 120 in contact with the tissue 110) are also insulated from the ambient environment to prevent heat loss and frost formation.

The heat transfer conduit 150 is connected to a heat exchanger 160 having a heat exchanger conduit (e.g., tubing) 161 that is positioned within or at least partially within the coolant vessel 140. The coolant vessel 140 contains a coolant 141 that is in close thermal contact with the heat exchanger 160, but is isolated from direct fluid contact with the heat transfer fluid 155 contained within the heat exchanger tubing 161. Accordingly, the heat exchanger 160 facilitates heat transfer between the heat transfer fluid 155 and the coolant 141, while preventing these fluids from mixing. As a result, the coolant 141 can be selected to have a composition different than that of the heat transfer fluid 155. In particular embodiments, the coolant 141 can be selected to have a phase transition temperature (from liquid/gel to solid) that is less than normal body temperature (about 37° C.) and in particular embodiments, in the range of from about 37° C. to about −20° C., or about 25° C. to about −20° C., or about 0° C. to about −12° C., or about −3° C. to about −6° C., to present a constant temperature environment to the heat transfer fluid 155 as the coolant 141 transitions from a solid to a liquid/gel. The heat transfer fluid 155 in such embodiments has a phase transition temperature that is less than that of the coolant 141. Accordingly, the heat transfer fluid 155 remains in a fluid state even when the coolant 141 or a portion of the coolant 141 is in a solid state. As a result, the heat transfer fluid 155 can flow within the heat transfer conduit 150 to convey heat away from the human tissue 110 even when the coolant 141 is frozen or at least partially frozen.

In operation, the device 100 can be prepared for use by placing the major components (e.g., the applicator 120, the heat transfer conduit 150, the heat exchanger 160 and the coolant vessel 140), as a unit, in a suitably cold environment. In a particular embodiment, the cold environment includes a freezer (e.g., a domestic freezer), in which the temperature typically ranges from about −10° C. to about −20° C., sufficient to freeze the coolant 141. After the coolant 141 is frozen, the device 100 can be removed from the freezer or other cold environment, as a unit, and the applicator 120 can be attached to the human tissue 110 using a cuff or other suitable attachment device (e.g., having a Velcro® closure, a buckle, or other releasable feature). Optionally, the user can apply a lotion between the applicator 120 and the skin to facilitate heat transfer and/or provide a moisturizing or other cosmetic effect. Whether or not the user applies a lotion or another intermediate constituent, the applicator 120 is positioned in thermal communication with the user's skin, so as to effectively remove heat from the lipid-rich tissue 112. The fluid driver 170 is then activated to drive the heat transfer fluid 155 through the heat transfer conduit 150, thus transferring heat from the subcutaneous lipid-rich tissue 112 to the frozen coolant 141 via the heat exchanger 160. As the coolant 141 melts, the temperature within the coolant vessel 140 remains approximately constant so as to provide a constant or nearly constant heat transfer fluid temperature to the human tissue 110. After the human tissue 110 has been cooled for an appropriate period of time, causing some or all of the coolant 141 to melt, the device 100 can be removed as a unit from the human tissue 110, as indicated by arrow A, and the coolant 141 can be re-frozen by placing the device 100 in the freezer. Accordingly, the cooling capacity of the coolant vessel 140 can be readily recharged or regenerated prior to a subsequent treatment process. The appropriate tissue-cooling period of time can be controlled by properly selecting the cooling capacity of the coolant 141, or via a controller and/or sensor, as described in further detail later with reference to FIG. 2.

In particular embodiments described above with reference to FIG. 1 and below with reference to FIGS. 2-8, the coolant 141 changes phase as it is heated by the heat transfer fluid 155, and then changes back again when it is cooled. In other embodiments, the coolant 141 can be heated and cooled without undergoing phase changes. For example, the coolant 141 can remain in a solid phase throughout both the heating and cooling processes, or can remain in a liquid phase throughout both processes. In such cases, the cooling process (whether it takes place in a freezer or other environment) does not freeze the coolant. When the coolant 141 remains a solid, its phase transition temperature is above that of the heat transfer fluid. When the coolant 141 remains a liquid, its phase transition temperature can be above, below, or equal to that of the heat transfer fluid 155. In such cases, the heat transfer fluid 155 and the coolant 141 can have different or identical compositions, while remaining isolated from direct fluid contact with each other.

Figure 2:
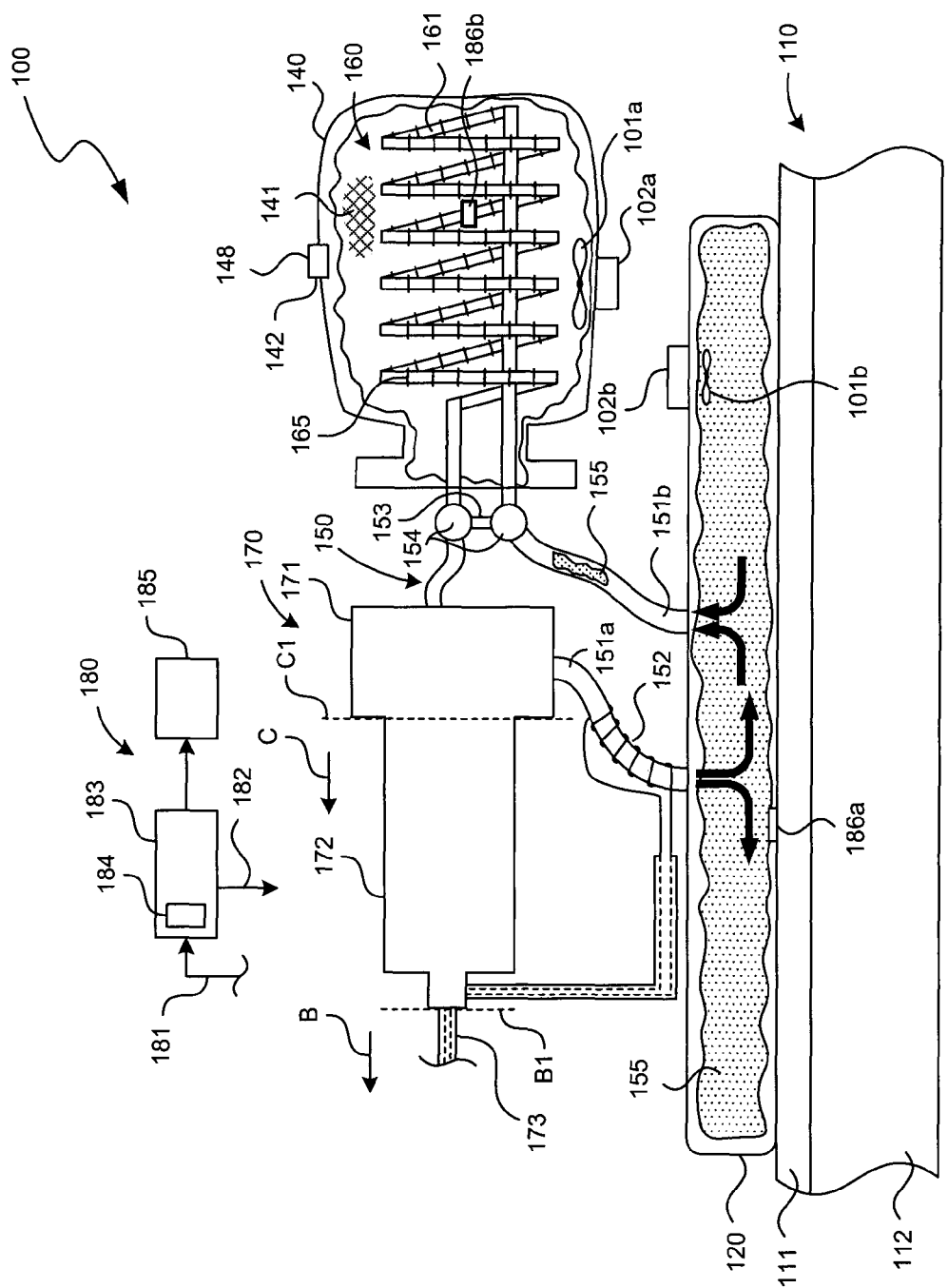
FIG. 2 is a partially schematic, partially cut-away illustration of a particular embodiment of the device shown in FIG. 1.

FIG. 2 is a partially schematic, partially cut-away illustration of an embodiment of the device 100 that operates in accordance with the general principles described above with reference to FIG. 1. Accordingly, the device 100 shown in FIG. 2 includes an applicator 120 and a coolant vessel 140 thermally connected to the applicator 120 via a heat exchanger 160 and a heat transfer conduit 150.

One characteristic of the device 100 shown in both FIG. 1 and FIG. 2 is that the when the applicator 120 is first placed against the human tissue 110, the heat transfer fluid 155 in the heat transfer conduit 150 and the applicator 120 will be at or approximately at the temperature of the cold environment in which the device 100 was placed. In at least some cases, this temperature may be uncomfortably low. Accordingly, the device 100 and associated methods can include features for reducing the likelihood that the user will encounter a potentially detrimental effect or uncomfortably cold sensation when first using the device 100. In a particular embodiment, the device 100 can include a heater 152 positioned to heat the heat transfer fluid 155 entering the applicator 120 via the supply portion 151a. This arrangement can increase the temperature of the heat transfer fluid 155 by at least an amount sufficient to reduce the user's discomfort and/or provide a safe and efficacious treatment. In a further particular aspect of this embodiment, the device 100 can be configured to shunt the heat transfer fluid 155 away from the heat exchanger 160 while the heat transfer fluid temperature is initially elevated. This arrangement can avoid unnecessarily melting the coolant 141 before treatment begins. Accordingly, the device 100 can include a shunt channel 153 connected between the supply portion 151a and the return portion 151b in parallel with the heat exchanger 160 to bypass the heat exchanger 160. One or more shunt valves 154 (two are shown in FIG. 2) are positioned to regulate flow through the shunt channel 153, e.g., to open or partially open the shunt channel 153 during initial startup, and then close or partially close the shunt channel 153 after the temperature of the applicator 120 has been elevated by a sufficient amount.

The device 100 can include a controller 180 to control the heater 152, the shunt valves 154, and/or other features of the device 100. For example, in a particular embodiment, the controller 180 includes a microprocessor 183 having a timer component 184. When the device 100 is initially powered (e.g., by activating the fluid driver 170), the microprocessor 183 can automatically open the shunt channel 153 via the shunt valves 154, and activate the heater 152. The heater 152 and the shunt channel 153 can remain in this configuration for a predetermined time, after which the microprocessor 153 automatically issues control signals deactivating the heater 152 and closing the shunt channel 153. Accordingly, the timer component 184 operates as a sensor by sensing the passage of time during which the heater 152 is actively heating the heat transfer fluid 155. In other embodiments described further below, one or more sensors can detect other characteristics associated with the device 100.

In a particular embodiment, the microprocessor 183 can direct the control signals 182 based on inputs 181 received from one or more temperature sensors. For example, the device 100 can include a first temperature sensor 186a positioned at the applicator 120. The microprocessor 183 can automatically activate the heater 152 and the shunt channel 153 until the first temperature sensor 186a indicates a temperature suitable for placing the applicator 120 against the human tissue 110. The device 100 can include a second temperature sensor 186b located at the coolant vessel 140 (e.g., the center of the coolant 141). The microprocessor 183 can accordingly direct control signals 182 that activate the fluid driver 170 for as long as the second temperature sensor 186b indicates a constant and/or suitably low temperature. When the second temperature sensor 186b identifies a temperature rise (indicating that the coolant 141 has completely melted), the microprocessor 183 can automatically deactivate the fluid driver 170. If the coolant 141 is not selected to change phase during heating and cooling, the micro-processor 183 can deactivate the fluid driver 170 when the temperature of the coolant 141 exceeds a threshold temperature. The controller 180 can include an output device 185 that indicates the operational modes or states of the device 100. For example, the output device 185 can display visual signals (e.g., via different colored LEDs) and/or aural signals (e.g., via an audio speaker) to signify when the applicator 120 is ready to be applied to the human tissue 110, when the treatment program is over, and/or when temperatures or other characteristics of any of the device components are outside pre-selected bounds.

In yet another embodiment, the controller 180 can direct a simplified process for handling the initial temperature of the heat transfer fluid 155. In particular, the controller 180 can monitor the temperature signal provided by the first temperature sensor 186a, without activating the fluid driver 170, and without the need for the heater 152 or the shunt channel 153. Instead, the controller 180 can generate an output (presented by the output device 185) when the ambient conditions cause the heat transfer fluid 155 to rise to an acceptable temperature, as detected by the first temperature sensor 186a. The user can optionally accelerate this process by applying heat to the applicator 120 and/or the heat transfer conduit 150 via an external heat source. An advantage of this approach is that it can be simpler than the integrated heater 152 described above. Conversely, the heater 152 (under the direction of the controller 180) can be more reliable and quicker, at least in part because the heater 152 is positioned within the insulation provided around the heat transfer conduit 150 and other device components.

The device 100 can include a variety of features configured to enhance uniform heat distribution and heat transfer. For example, the heat exchanger 160 can include fins 165 on the heat exchanger tubing 161 to increase the surface area available to transfer heat between the heat transfer fluid 155 and the coolant 141. The coolant vessel 140 can also include a first agitator 101a that distributes the melting coolant 141 within the coolant vessel 140 to provide for a more uniform temperature and heat transfer rate within the vessel 140. In one embodiment, the first agitator 101a can include a magnetically driven device, and can be magnetically coupled to a first actuator motor 102a positioned outside the coolant vessel 140. Accordingly, the agitator 101a can operate without the need for a sealed drive shaft penetrating into the coolant vessel 140. A similar arrangement can be used at the applicator 120. In particular, the applicator 120 can include a second agitator 101b driven by a second actuator motor 102b to distribute the heat transfer fluid 155 uniformly within the applicator 120. Suitably positioned internal fluid channels can be used in addition to or in lieu of the second agitator 101b to uniformly distribute the heat transfer fluid 155 in the applicator 120. A representative device that includes such features is a Model No. 10240 pad, available from Breg Polar Care (bregpolarcare.com). The actuator motors 102a, 102b can be operatively coupled to a power cord 173, which also provides power to the fluid driver 170 and the heater 152. In other embodiments, the device 100 can include other elements that agitate and/or distribute the fluid in the applicator 120 and/or the coolant vessel 140. Such elements can include liquid jets, shaft-driven stirrers, pistons and/or other devices that move the solid and/or liquid portion of the coolant 141 within the coolant vessel 140, and/or actuators that vibrate, shake, tip or otherwise move the coolant vessel 140 itself or heat exchanger 160 within the coolant vessel.

As noted above, the applicator 120, the heat transfer conduit 150, the heat exchanger 160, and the coolant vessel 140 can be moved as a unit between the target tissue 110 and a freezer or other cold environment prior to and after treatment. In a particular embodiment, the remaining components or elements of the device 100 shown in FIG. 2 can also be placed in the freezer. For example, when the fluid driver 170 includes a pump 171 driven by a pump motor 172, these components (along with the controller 180) can also be placed in the freezer. In other embodiments, one or more of these components may be removed prior to placing the rest of the device 100 in the freezer. For example, the power cord 173 can be removed from the motor 172 and other system components at a junction B1 as indicated by arrow B. In another embodiment, the pump motor 172 can be removed from the device 100 at a junction C1 as indicated by arrow C. For example, the pump motor 172 can be magnetically coupled to the pump 171, generally in the manner of the stirrers described above to make connecting and disconnecting the motor 172 easier. In still another aspect of this embodiment, the controller 180 and/or components of the controller 180 can be carried by the motor 172 and can accordingly be removed from the device 100 along with the motor 172.

Certain features described above in the context of a processor-based automatic control system can, in other embodiments, operate without a processor, or can operate manually. For example, the shunt valves 154 can include thermostatic radiator values, or similar valves that have an integrated temperature sensor (e.g., a mechanical thermostat) that autonomously drives the valve without the need for a processor. In other embodiments, the coolant 141 can change color as it undergoes its phase change, which can eliminate the need for the second temperature sensor 186b. In one aspect of this embodiment, the coolant vessel 140 is transparent, allowing the user to readily see both when the coolant 141 is frozen and when the coolant 141 has melted. In the event the device 100 loses coolant 141 over the course of time, the coolant vessel 140 can include a fill/drain port 142. In a particular aspect of this embodiment, the fill/drain port 142 can have a removable plug 148 that is transparent, in addition to or in lieu of the coolant vessel 140 being transparent. Similarly, the heat transfer fluid 155 can include constituents that change color when the heat transfer fluid attains a temperature that is no longer suitable for properly chilling the tissue 110. The applicator 120 and/or the heat transfer conduit 150 (or portions thereof) can be made transparent to allow the user to easily determine when this temperature threshold has been exceeded.

Both the coolant 141 and the heat transfer fluid 155 are selected to be highly thermally conductive. Suitable constituents for the coolant 141 include water in combination with propylene glycol, ethylene glycol, glycerin, ethanol, isopropyl alcohol, hydroxyethyl cellulose, salt, and/or other constituents. In at least some embodiments, the same constituents can be used for the heat transfer fluid 155, but the ratios of the constituents (and therefore the overall composition of the heat transfer fluid) are selected to produce a lower liquid/solid phase transition temperature. Both the heat transfer fluid 155 and the coolant 141 can be selected to have high heat conductivity and low toxicity in case of a leak. Both can include an anti-microbial agent to restrict or prevent algae formulation and/or propagation of other undesirable life forms. The coolant 141 can be selected to have a high heat capacity to better absorb heat from the heat transfer fluid 155. The heat transfer fluid 155 can have a relatively low heat capacity so that it readily heats up when the heater 152 is activated. The heat transfer fluid 155 can also be selected to have a low viscosity at operating temperatures to facilitate flow through the heat transfer conduit 150, the heat exchanger 160 and the applicator 120. In any of these embodiments the coolant vessel 140 in which the coolant 141 is disposed can be flexible and elastic, and/or can include a vent or other feature to accommodate volume changes as the coolant 141 changes phase.

Figure 3:
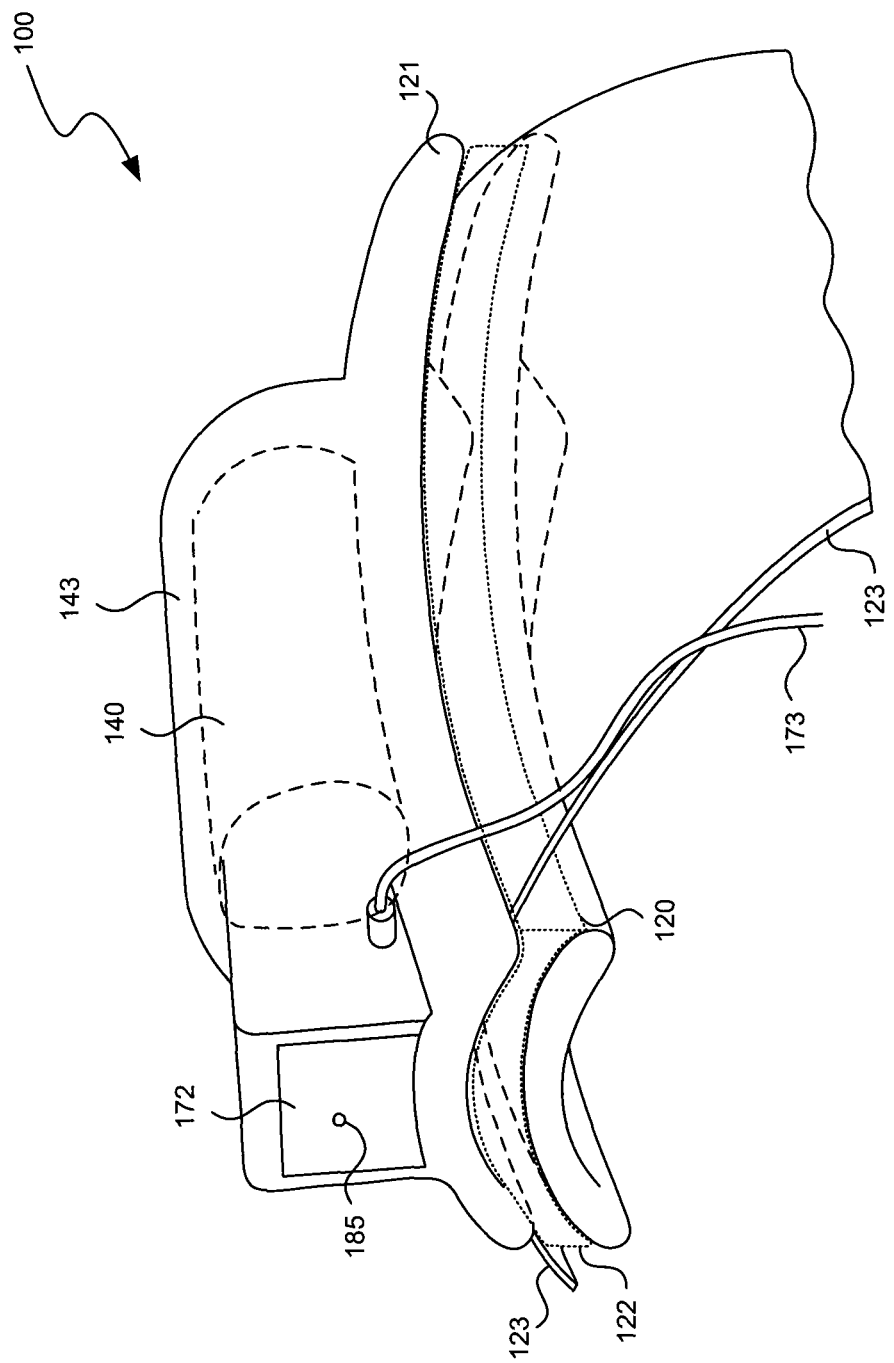
FIG. 3 is a partially schematic illustration of a device having an overall arrangement generally similar to that shown in FIG. 1, configured in accordance with still another embodiment of the disclosure.

FIG. 3 is a partially schematic, isometric illustration of an embodiment of the device 100 described above with reference to FIG. 2. As shown in FIG. 3, the applicator 120 has a generally flexible configuration, allowing it to conform to the shape of the tissue to which it is applied. An attachment device 123 releasably attaches the applicator 120 to the tissue and can accordingly include a strap (e.g. Velcro), a cuff (e.g., generally similar to a blood pressure cuff) or another suitable device. The coolant vessel 140 is housed in a coolant vessel housing 143 that is in turn attached to or otherwise includes the support structure 121. The support structure 121 can be at least partially flexible so that when it is attached to the applicator 120, it does not overly inhibit the ability of the applicator 120 to conform to the human tissue. In one embodiment, the support structure 121 and the coolant vessel housing 143 can be supported relative to the applicator 120 with standoffs. In another embodiment, an optional foam or other flexible layer (e.g. an inflatable air bladder) 122 can be positioned between the support structure 121 and the applicator 120 to further facilitate the ability of the applicator 120 to flex relative to the coolant vessel housing 143.

In one aspect of an embodiment shown in FIG. 3, the power cord 173 can be releasably attached directly to the pump motor 172, thus allowing the power cord 173 to be removed before the device 100 is placed in the freezer. The power cord 173 can be connected directly to an AC outlet, and can include a DC converter if the pump motor 172 is a DC motor. If the pump motor 172 is coupled to a rechargeable battery located within the housing 143, the power cord 173 can be used to recharge the battery.

In another aspect of this embodiment, the pump motor 172 itself can be removed from the coolant vessel housing 143, along with the power cord 173, generally in the manner described above with reference to FIG. 2. In still a further particular aspect of this embodiment, the controller 180 (not visible in FIG. 3) and associated output device 185 can be carried by the pump motor 172 and can accordingly be readily removed from the coolant vessel housing 143 along with the pump motor 172.

One feature of particular embodiments of the device 100 described above with reference to the FIGS. 1-3 is that the applicator 120, the coolant vessel 140, the heat exchanger 160, and the heat transfer conduit 150 can be configured as an inseparable unit (at least during normal use—components may be separated by an authorized servicer if necessary during a maintenance or repair process). Accordingly, these components form a sealed, closed-loop path for the heat transfer fluid 155. An advantage of this feature is that it is simple to use. In particular, the user can place the entire device 100 (or at least the above components) in the freezer or other cold environment until the coolant 141 is frozen, and can remove the entire device 100 as a unit from the freezer or other cold environment prior to cooling the target tissue. Because the arrangement is simple to use, it can be particularly suitable for home use. Because it does not include removable components (in certain embodiments) or separable fluid connections, it is expected to be more robust than systems that do include such features. Because the coolant 141 has a fixed liquid/solid phase transition temperature, the device 100 can easily control the temperature of the heat transfer fluid 155 with a reduced level of active control, and the device 100 can be thermally recharged in any environment having a temperature less than the phase transition temperature.

Another feature of particular embodiments of the device 100 described above is that the volume of heat transfer fluid 155 contained in the system can be made relatively low by using short lengths and/or small diameters for the heat transfer conduit 150 and the heat exchanger tubing 161, and a low (e.g., thin) profile for the applicator 120. Accordingly, the coolant 141 can more quickly cool the heat transfer fluid 155 and the entirety of the effective heat transfer surface of the applicator 120. Having a low thermal mass for the heat transfer fluid 155 will also reduce the amount of time and/or energy required to elevate the temperature of the applicator 120 to a comfortable level after the device 100 has been removed from the freezer.

Still another feature of particular embodiments of the device 100 described above is that the unitary arrangement of the device is expected to produce a compact size and therefore low mass. These features in turn can make it easier to position the device in a freezer (e.g., a domestic freezer), and can make the device more comfortable and convenient to wear during use.

Yet another feature of at least some of the foregoing embodiments is that the simplicity of the device can reduce manufacturing costs and therefore the costs to the user. In at least some instances, the device need not include the serviceable component features described above because the device may be cheaper to replace than repair. The device can include an automated lock-out or shut-down feature that activates after a pre-determined number of uses to prevent use beyond an expected period of threshold efficacy or useful life.

Figure 4:
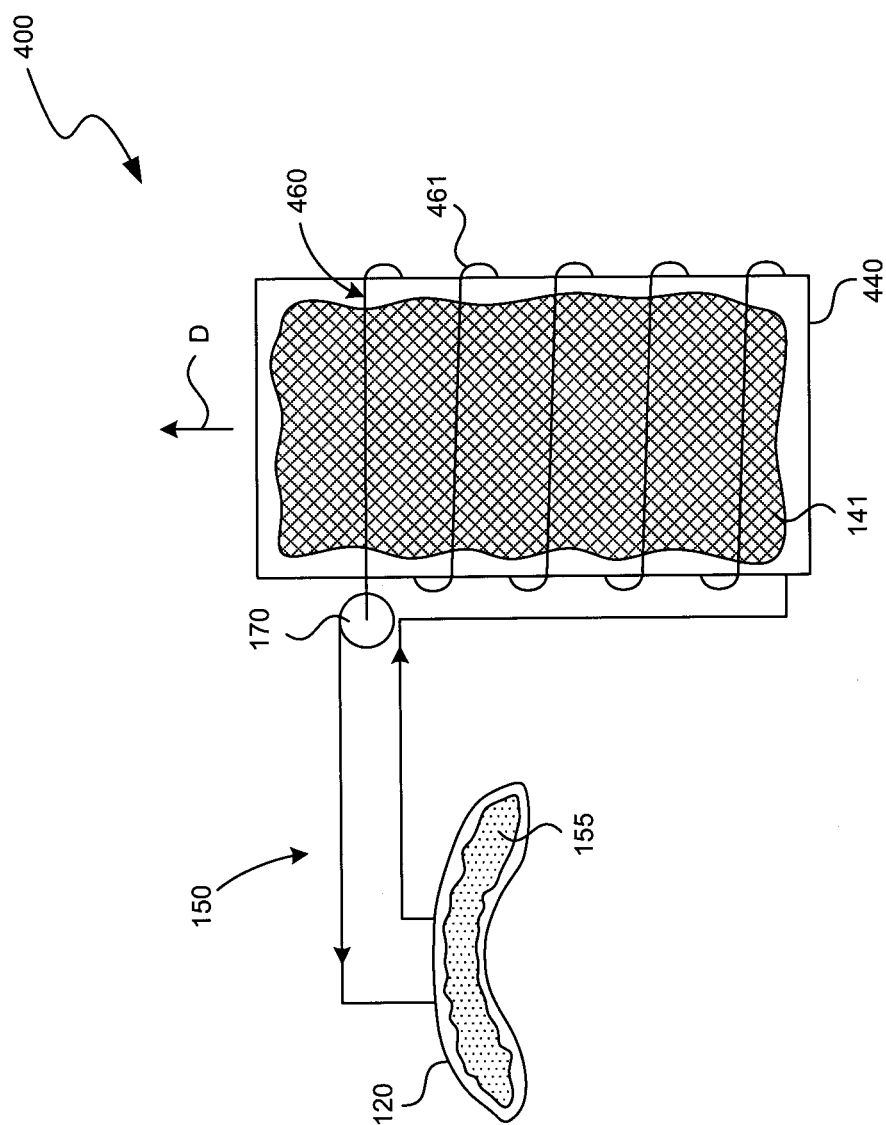
FIG. 4 is a partially schematic illustration of a device having a heat exchanger and a removable coolant vessel configured in accordance with another embodiment of the disclosure.

3. Representative Devices and Methods that Include Separable Coolant Vessels FIG. 4 is a partially schematic, partially cut-away illustration of an embodiment of a device 400 having a user-removable or separable coolant vessel 440, unlike the configurations described above with reference to FIGS. 1-3. In particular, the device 400 can include a heat exchanger 460 having a heat exchanger conduit (e.g., tubing) 461 positioned external to the coolant vessel 440, allowing the coolant vessel 440 to be removed from the device 400 (as indicated by arrow D) for thermal recharging or regeneration. Accordingly, the coolant vessel 440 can be placed in a cold environment (e.g., a freezer) to re-cool (e.g., re-freeze) the coolant 141, without placing the entire device 400 in the cold environment. This arrangement may be suitable for applications in which freezer space is limited and thus placing only the coolant vessel 440 in the freezer is advantageous. As a result, certain aspects of the device 400 can be simpler than the device 100 described above with reference to FIGS. 1-3. For example, the heat transfer conduit 150 is not cooled along with the coolant vessel 440 and accordingly the need for the heater 152 and/or shunt channel 153 and shunt valves 154 described above with reference to FIG. 2 can be eliminated. Conversely, an advantage of the arrangement described above with reference to FIGS. 1-3 is that the interface between heat exchanger tubing 161 and the coolant vessel 140 need not be disturbed when the coolant vessel 140 is chilled. As described further below with reference to FIGS. 5A-6B, certain aspects of the device 400 are designed to mitigate the potential impact of detaching and reattaching the heat exchanger 460 and the coolant vessel 440.

Figure 5A:
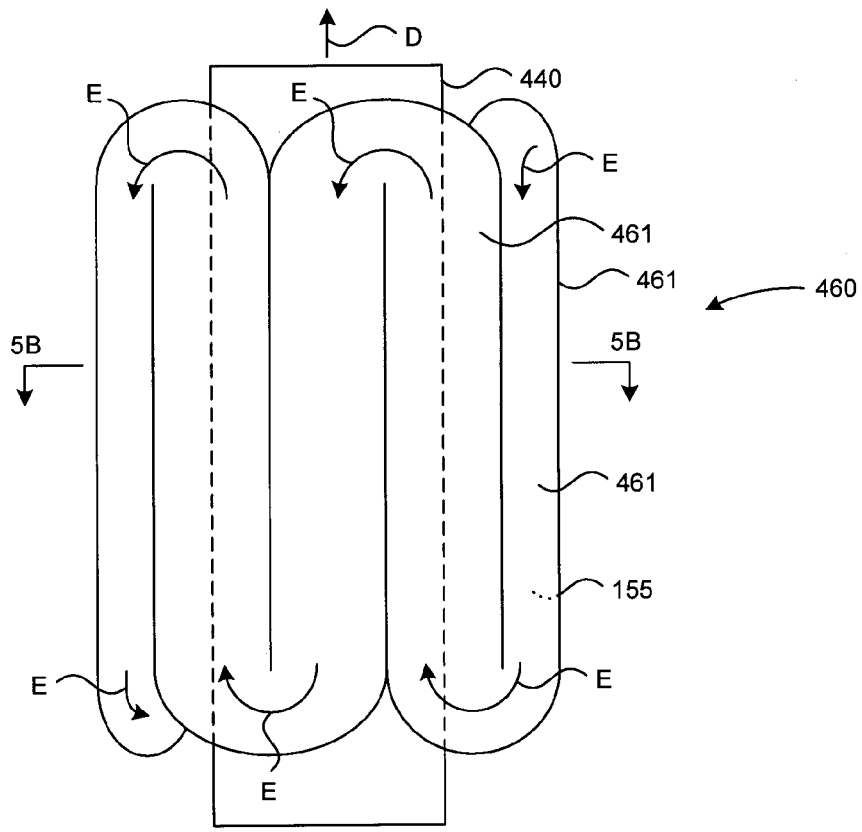
FIG. 5A is a partially schematic, enlarged illustration of an embodiment of the coolant vessel and heat exchanger shown in FIG. 4.

FIG. 5A is an enlarged, partially schematic illustration of an embodiment of the coolant vessel 440 and the heat exchanger 460 in which the heat exchanger tubing 461 is positioned around the outside of the coolant vessel 440. In particular, the heat exchanger tubing 461 can have a serpentine shape extending upwardly and downwardly along the longitudinal axis of the coolant vessel 440. The heat transfer fluid 155 passes through the heat transfer tubing 461 as indicated by arrows E. To remove the coolant vessel 440 from the heat exchanger 460, the user pulls the coolant vessel 440 upwardly as indicated by arrow D in FIG. 5A. The heat exchanger tubing 461 can be "springy" and can accordingly be resiliently biased inwardly toward the coolant vessel 440 to releasably secure the coolant vessel 440 in position, and to provide intimate thermal contact between the heat exchanger tubing 461 and the exterior surface of the coolant vessel 440. This feature can also promote a "scrubbing" mechanical contact between the heat exchanger tubing 461 and the exterior surface of the coolant vessel 440 to remove frost build-up or other residue to ensure good thermal contact as these components are connected. Further details of the foregoing arrangement are described below with reference to FIG. 5B.

Figure 5B:
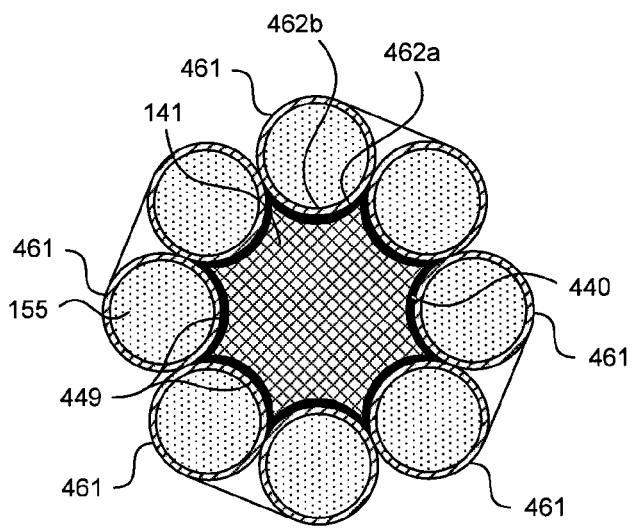
FIG. 5B is a partially schematic, cross-sectional illustration of the heat exchanger and coolant vessel taken substantially along line 5B-5B of FIG. 5A.

FIG. 5B is a partially schematic, cross-sectional illustration of the heat exchanger 460 and the coolant vessel 440, taken substantially along line 5B-5B of FIG. 5A. As shown in FIG. 5B, the coolant vessel 440 can have an outer surface with a series of recesses 449, each of which is sized and positioned to receive a portion of the heat exchanger tubing 461. The exterior surface of the coolant vessel 440 can include a first thermally conductive surface 462a that is in intimate thermal and physical contact with a corresponding second thermally conductive surface 462b of the heat exchanger tubing 461. Accordingly, this arrangement can readily transfer heat between the heat transfer fluid 155 within the heat exchanger tubing 461, and the coolant 141 within the coolant vessel 440. The coolant vessel 440 can include features for uniformly distributing the liquid portion of the coolant 141 (e.g., agitators) in a manner generally similar to that described above with reference to FIG. 2.

Figure 6A:
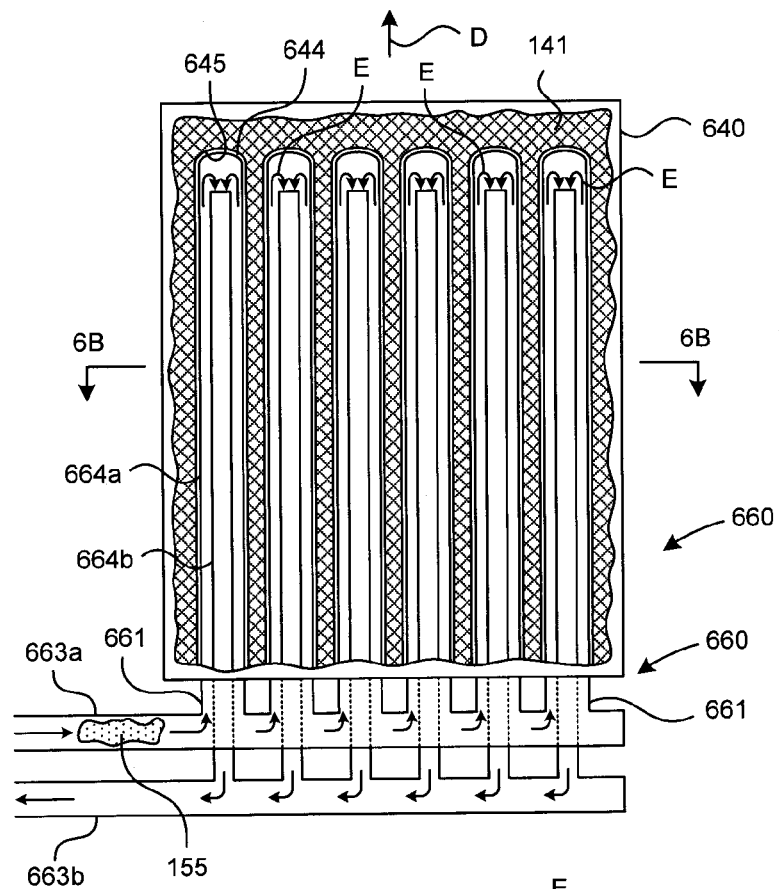
FIG. 6A is a partially schematic, partially cut-away illustration of a coolant vessel and heat exchanger configured in accordance with another embodiment of the disclosure.
Figure 6B:
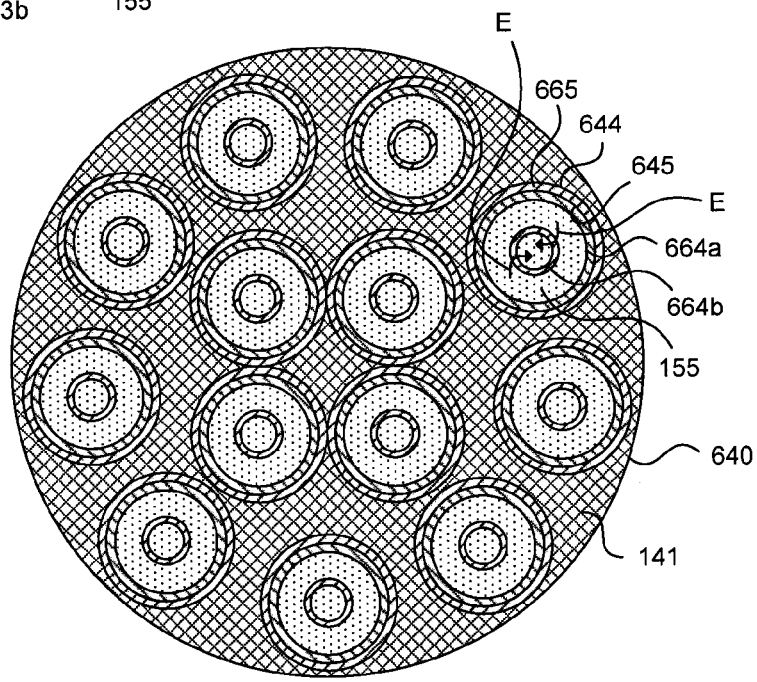
FIG. 6B is a partially schematic, cross-sectional illustration of an embodiment of the heat exchanger and coolant vessel, taken substantially along line 6B-6B of FIG. 6A.

FIGS. 6A and 6B illustrate another arrangement of a coolant vessel 640 that is removably attached to a corresponding heat exchanger 660 in accordance with another embodiment of the technology. In one aspect of this embodiment, the coolant vessel 640 includes multiple vertically extending blind channels 644 defined at least in part by a thermally conductive channel wall 645. The heat exchanger 660 includes thermally conductive heat exchanger tubing 661 that directs the heat transfer fluid 155 into and out of the blind channels 644. In particular, the heat exchanger tubing 661 can include supply sections 664a that extend into the blind channels 644 and are coupled to a supply manifold 663a. The heat exchanger tubing 661 can further include corresponding return sections 664b that also extend into each of the blind channels 644 and are coupled to a return manifold 663b. In a particular embodiment, the return sections 664b are located annularly inwardly within the corresponding supply sections 664a. Accordingly, the heat transfer fluid enters the supply sections 664a, rises within the blind channels 664 and then descends through the return sections 664b, as indicated by arrows E. The coolant vessel 640 is removed from the heat exchanger 660 by pulling it upwardly away from the heat exchanger 660 as indicated by arrow D, and is replaced by placing it downwardly over the heat exchanger 660, with the blind channels 644 aligned with the corresponding supply sections 664a. The blind channels 644 and the corresponding supply sections 664a can be tapered and/or otherwise biased into contact with each other to promote thermal contact and to facilitate mechanically scraping frost from surfaces of either element.

FIG. 6B is a partially schematic, cross-sectional illustration of the coolant vessel 640 and the heat exchanger 660, taken substantially along line 6B-6B of FIG. 6A. As shown in FIG. 6B, the blind channels 664 include thermally conductive channel walls 665 that are in intimate thermal contact with the outer surfaces of the supply sections 664a. Arrows E indicate the radially inward path of the heat transfer fluid 155 as it moves from the supply sections 664a to the return sections 664b.

Figure 7:
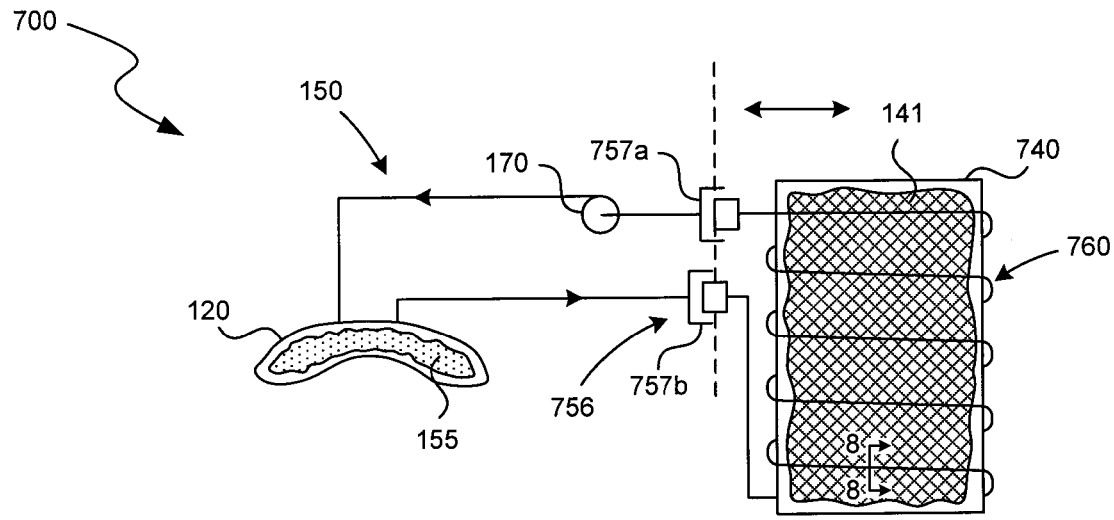
FIG. 7 is a partially schematic illustration of a device having a coolant vessel and heat exchanger that are separable from an applicator in accordance with yet another embodiment of the disclosure.

4. Representative Devices and Methods that Include Separable Coolant Vessels and Heat Exchangers FIG. 7 is a partially schematic, partially cut-away illustration of a device 700 having a releasable coupling 756 between a heat exchanger 760 and a coolant vessel 740 on one hand, and the heat transfer conduit 150 on the other. Accordingly, the releasable coupling 756 can include a supply coupling 757a at the supply portion 151a of the heat transfer conduit 150, and a return coupling 757b at the return portion 151b of the heat transfer conduit 150. The couplings 757a, 757b can include any suitable fluid-tight, easily releasable and reattachable elements. For example, the couplings 757a, 757b can include quick-release couplings generally similar to those used for intravenous fluid connections.

One feature of an embodiment shown in FIG. 7 is that, like the embodiments described above with reference to FIGS. 4-6B, the entire device 700 need not be placed in the freezer or other cold environment to re-solidify or otherwise re-cool the coolant 141. In addition, the device 700 does not require that the thermal connection between the heat exchanger 760 and the coolant vessel 740 be disturbed in order to recharge the coolant vessel 740. Conversely, an advantage of the arrangements described above with reference to FIGS. 1-6B is that they do not require connecting and disconnecting fluid conduits.

Figure 8:
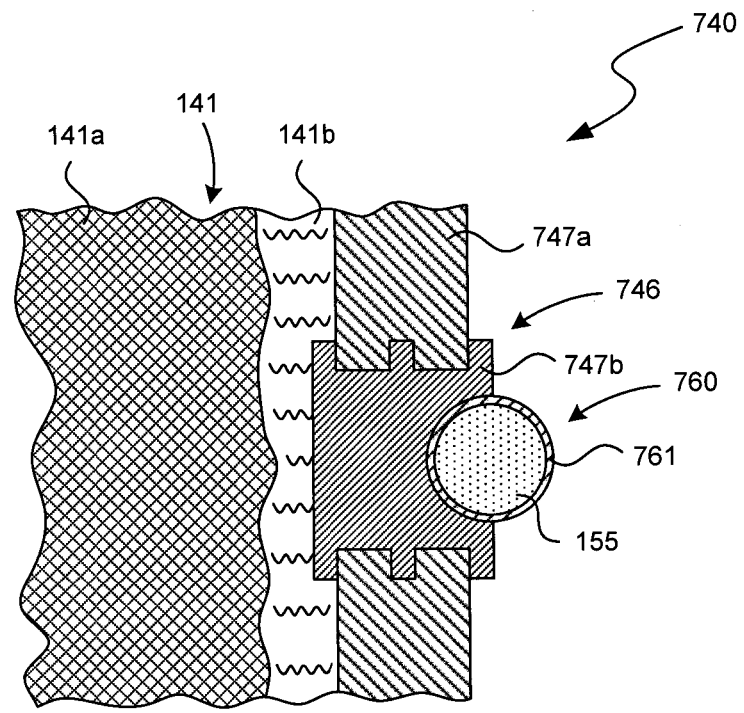
FIG. 8 is a partially schematic illustration of a portion of the coolant vessel and heat exchanger, taken substantially along line 8-8 of FIG. 7.

FIG. 8 is a partially schematic, cross-sectional illustration of a portion of the heat exchanger 760 and the coolant vessel 740, taken substantially along line 8-8 of FIG. 7. As shown in FIG. 8, the coolant vessel 740 can include a vessel wall 746 having an insulative portion 747a over a portion of its surface, and a conductive portion 747b in areas adjacent to the heat exchanger tubing 761. For example, the insulative portion 747a can include a material such as a plastic that has a low thermal conductivity to prevent or at least restrict heat transfer to the coolant vessel 740 except as it is received from the heat exchanger tubing 761. The conductive portion 747b can include copper or another highly thermally conductive material that readily transfers heat between the coolant 141 and the heat exchanger tubing 761, which can also include copper or another highly thermally conductive material. The heat exchanger tubing 761 can be welded to or otherwise intimately bonded to the conductive portion 747b in a way that provides high thermal conductivity between the two. In other embodiments, the heat exchanger tubing 761 can take the form of a channel that is integrally formed with the conductive portion 747b, e.g., in a casting process.

When the coolant 141 is selected to undergo a phase change during operation, it can include a solid component 141a generally positioned away from the vessel wall 746 once the coolant 141 begins to melt, and a liquid component 141b generally in contact with the inner surface of the vessel wall 746 and conductive portion of the vessel wall 747b. As described above, the coolant vessel 740 can include an agitator or other device to enhance the uniform distribution of heat transfer within the coolant vessel 740 by circulating the liquid component 141b, moving the solid component 141a, and/or vibrating or otherwise moving the coolant vessel 740.

5. Representative Applicators and Associated Methods

Figure 9:
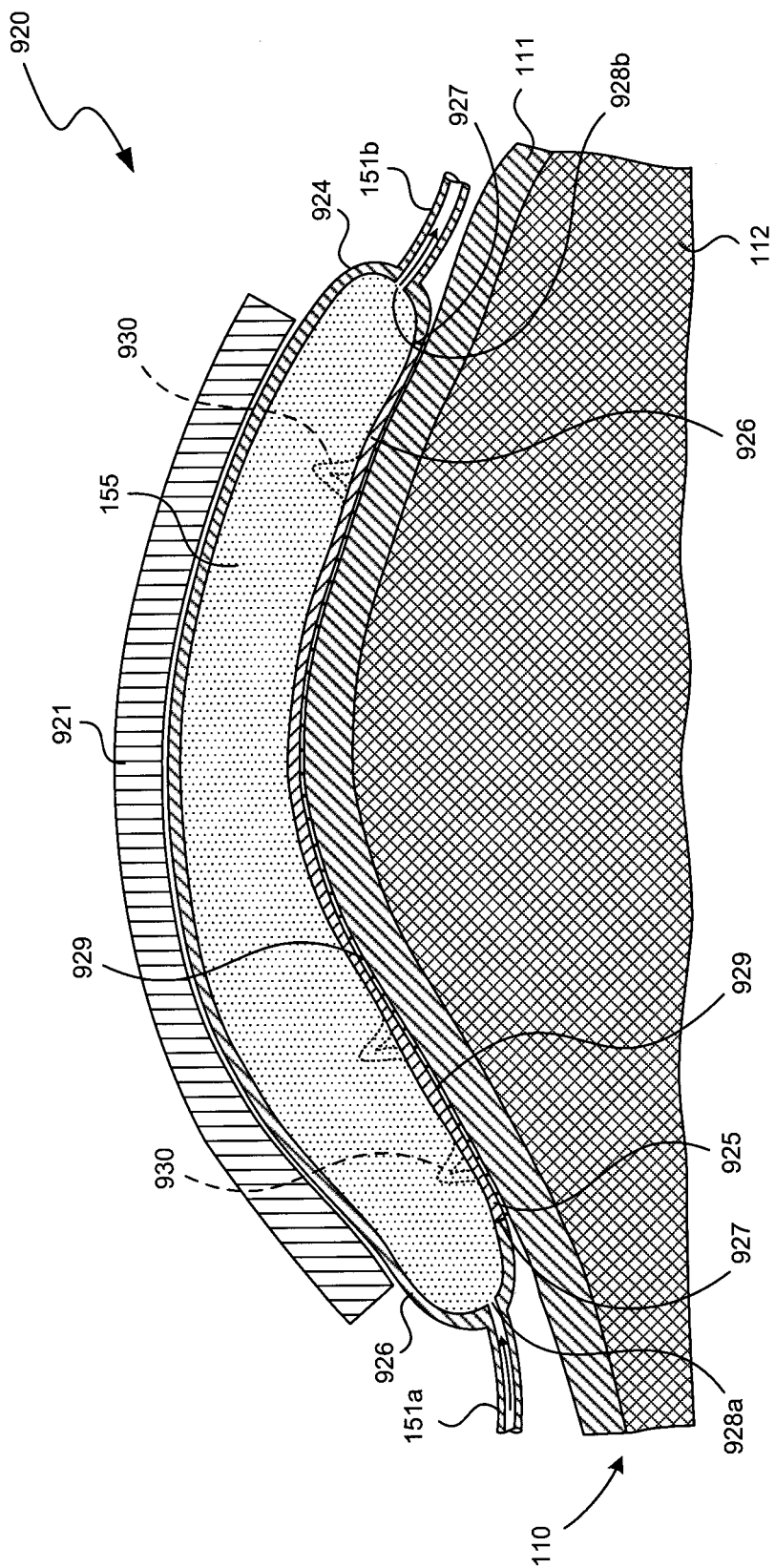
FIG. 9 is a partially schematic, cross-sectional illustration of an applicator having non-elastic and elastic materials arranged in accordance with an embodiment of the disclosure.
Figure 10:
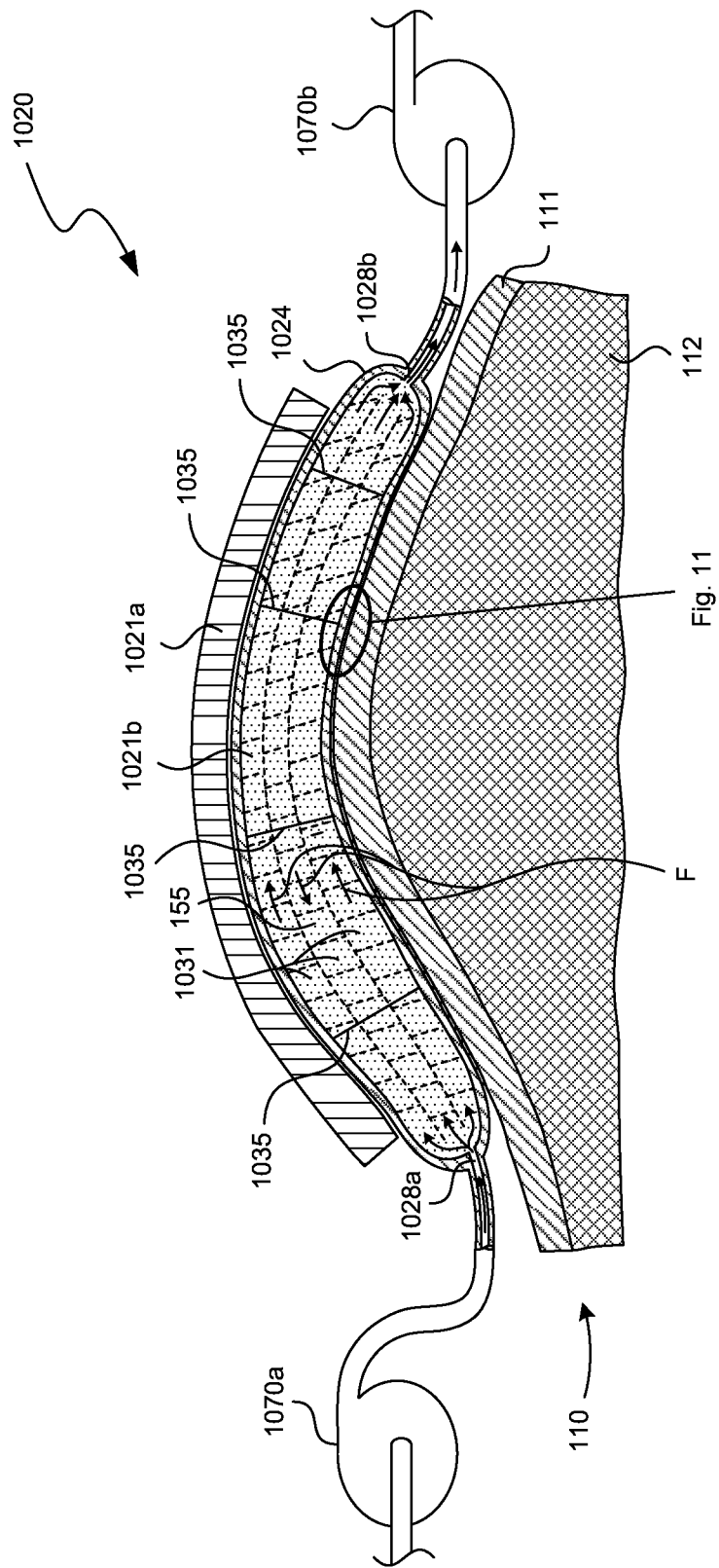
FIG. 10 is a partially schematic, cross-sectional illustration of an applicator having an internal support structure in accordance with an embodiment of the disclosure.
Figure 11:
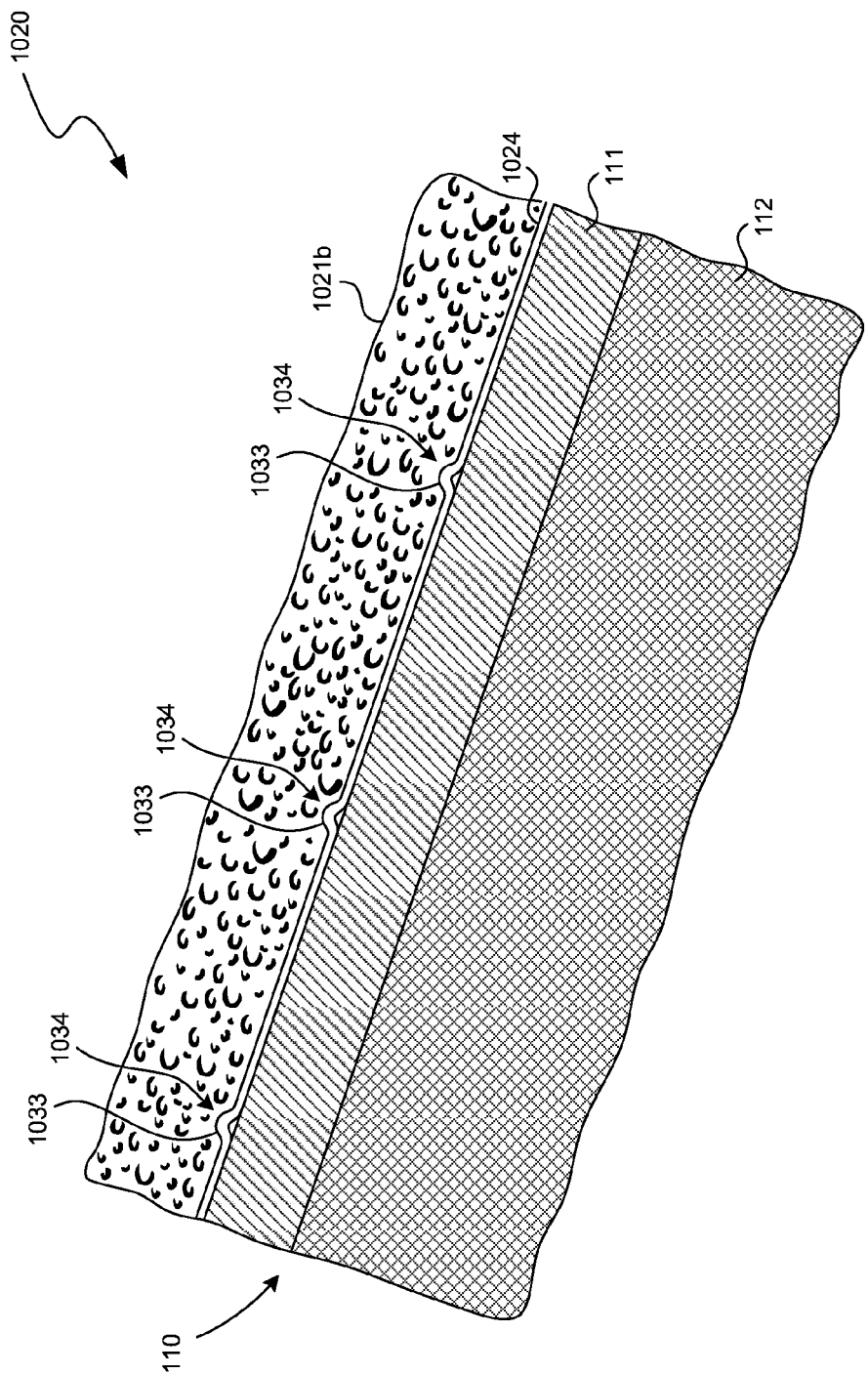
FIG. 11 is an enlarged illustration of a portion of the applicator shown in FIG. 10.

FIGS. 9-11 illustrate particular features of applicators that may form a portion of any of the devices described above with reference to FIGS. 1-8. In other embodiments, these applicators may be used with devices other than those expressly shown and described above with reference to FIGS. 1-8. The size and shape of the applicator can be selected based on the user's physiology and the location on the user's body to which the applicator will be attached.

FIG. 9 illustrates an applicator 920 that includes an envelope 924 having an entry port 928a coupled to a heat transfer fluid supply portion 151a, and an exit port 928b coupled to a return portion 151b. The envelope 924 can include a flexible first portion 925 in contact with the human tissue 110, and a flexible second portion 926 facing away from the human tissue 110. The flexible first portion 925 can be attached to the flexible second portion 926 at corresponding bonds 927 formed by an adhesive, thermal welding, or other suitable process. The first portion 925 has a first elasticity, and the second portion 926 has a second elasticity less than the first elasticity. Accordingly, the second portion 926 can, in at least some embodiments, be non-elastic. As used herein, the term "non-elastic" applies to a material that does not stretch, or stretches by only an insignificant amount when the applicator 920 is subjected to normal operating pressures. The term "elastic" as used herein applies to a material that does stretch when the applicator is subjected to normal operating pressures provided by the attachment of the device to the patient and/or heat transfer fluid 155. Because the first portion 925 is more elastic than the second portion 926, it can readily conform to the local shape of the human tissue 110. In particular, the first portion 925 can conform to the underlying tissue 110 without forming creases 930 (shown in dotted lines in FIG. 9), which form in some existing devices and can interfere with skin/applicator thermal contact and/or internal flow within the applicator 920. As a result, the first portion 925 is more likely to remain in close thermal contact with the human tissue 110 and can therefore more efficiently transfer heat away from the tissue 110. The second portion 926 can flex in a manner that accommodates the contour of the human tissue 110, without stretching at all, or without stretching in a manner that might cause the envelope to bulge outwardly away from the tissue 110 (e.g., at the ends of the applicator 920) and thereby reduce the degree of thermal contact between the envelope 924 (and more particularly, the heat transfer fluid 155) and the tissue 110.

In particular embodiments, the second portion 926 can include polyethylene, polypropylene, nylon, vinyl, and/or another suitable plastic film. The first portion 925 can include latex rubber, nitrile, polyisoprene and/or urethane, and/or another suitable elastomeric material. An optional elastic mesh 929 can be positioned adjacent to the first portion 925 (or the entire envelope 924), and can include an elastic nylon, rubber and/or other suitable elastic material. The mesh 929 can prevent the first portion 925 from undergoing excessive wear and/or bulging during handling. It can accordingly be strong, but thin enough to avoid significantly interfering with the heat transfer process between the applicator 920 and the tissue 110.

In a particular embodiment, the applicator 920 can also include a flexible support structure 921 that provides additional support for the envelope 924, without inhibiting the ability of the envelope 924 to conform to the tissue 110. The support structure 921 can also function as the releasable coupling (e.g., a cuff) securing the applicator 920 to the tissue 110. In any of these embodiments, the support structure 921 can have a pre-formed shape (e.g., a downwardly-facing concave shape) and can be resiliently biased toward the pre-formed shape. Accordingly, the applicator 920 can more readily conform to a convex tissue surface. In particular embodiments, a family of applicators having different shapes can be coupled to a similar type of overall cooling device to provide for system commonality and interchangeability.

FIG. 10 is a partially schematic, cross-sectional illustration of an applicator 1020 having an envelope 1024, an external support structure 1021a generally similar to that described above with reference to FIG. 9, and an internal support structure 1021b located within the envelope 1024. The internal support structure 1021b can be porous, e.g., 50% porosity or higher in some embodiments, and in particular embodiments, in the range of from about 75% porosity to about 95% porosity. Accordingly, the internal support structure 1021b can diffuse the heat transfer fluid 155 throughout the envelope 1024 from an entry port 1028a to an exit port 1028b, without overly restricting the flow of the heat transfer fluid 155. The particular porosity value selected for the internal support structure 1021b can depend on factors that include the viscosity and/or flow rate of the heat transfer fluid 155. In a particular embodiment, the internal support structure 1021b can include a porous matrix material having one or multiple layers 1031 (three are shown in FIG. 10 for purposes of illustration) that can slide relative to each other, as indicated by arrows F. In a further particular embodiment, the internal support structure 1021b is attached to the inner surfaces of the envelope 1024 to prevent the envelope from overly stretching. The envelope 1024 can also include spaced-apart connections 1035 (e.g., stitches or perforated panels) that extend from the envelope upper surface through the internal support structure 1021b to the envelope lower surface to prevent or restrict the envelope 1024 from ballooning when pressurized with the heat transfer fluid 155 while allowing the layers 1031 to slide laterally relative to each other. Accordingly, when the applicator 1020 is coupled to an upstream fluid driver 1070a, the pressure exerted by the incoming heat transfer fluid 155 on the envelope 1024 will be less likely to expand the envelope 1024.

The internal support structure 1021b can resist buckling, in addition to or in lieu of resisting bulging or ballooning. For example, the internal support structure 1021b can have a high enough buckling strength so that when the applicator 1020 is coupled to a downstream fluid driver 1070b, the envelope 1024 will not collapse upon itself due to external, ambient pressure (e.g., to the point that it inhibits the flow of heat transfer fluid 155) when the heat transfer fluid 155 is withdrawn through the exit port 1028b. In particular embodiments, the heat transfer fluid 155 may be withdrawn via a pressure that is up to about 2 psi below the pressure outside the envelope 1024. In other embodiments, the foregoing pressure differential can be up to about 5 psi or 10 psi without the envelope 1024 collapsing on itself. This will help keep the envelope from ballooning due to positive internal pressure. Another advantage of the downstream fluid driver 1070b is that if the envelope 1024 is inadvertently punctured, the downstream fluid driver 1070b will suck air through the puncture, while the upstream fluid driver 1070a will continue to pump heat transfer fluid 155 through such a puncture.

FIG. 11 is a partially schematic, enlarged illustration of a portion of the applicator 1020 circled in FIG. 10. As shown in FIG. 11, the internal support structure 1021b can include small pores 1034 distributed throughout the structure. At the interface with the tissue 110, the pores can form a distributed arrangement of generally hemispherical dimples. When the envelope 1024 includes a material that is not elastic, the material will tend to crease when folded over a convex portion of the tissue 110. The pores 1034 are small enough so that they accommodate or receive small "microcreases" 1033 that can form along the surface of the envelope 1024. Unlike the creases 930 described above with reference to FIG. 9, the microcreases 1033 are very small and accordingly do not significantly inhibit the internal flow within the applicator and do not significantly disrupt the uniformity of the heat transfer between the heat transfer fluid 155 within the envelope 1024, and the tissue 110 outside the envelope 1024. In effect, the microcreases 1033 can distribute the creasing effect of the envelope material over a larger area that reduces the overall impact of the effect on fluid flow and heat transfer. In particular embodiments, the microcreases 1033 can have a generally hemispherical shape that is pre-set into the envelope material using a thermoset process. In other embodiments, the shape and/or formation process of the microcreases 1033 can be different. In still another embodiment, the entire portion of the envelope 1024 in contact with the patient tissue can have a pre-set or pre-formed shape (e.g., a hemispherical or other concave shape) that is maintained as the envelope is placed in contact with the patient tissue;

In a particular embodiment, the internal support structure 1021b can include a TN Blue non-abrasive non-woven polyester pad available from Glit/Microtron. This material can be made in multiple layers (e.g., two layers, each 0.35 of an inch thick) encased in a polyether-polyurethane film envelope 1024 having a thickness of 0.006-0.012 inches. The internal support structure 1021b, which is already porous due to the fibrous make-up of the material, can be even further perforated with a hole pattern, producing small diameter holes spaced uniformly spaced apart, and oriented generally perpendicular to the major surfaces of the envelope 1024. These holes can facilitate bending the internal support structure 1021b to conform to convex and/or concave shapes. It is expected that the relatively thin overall dimensions of the resulting applicator 1020 (e.g., from about 0.25 inch to about 0.50 inch) will allow the applicator 1020 to readily conform to the human anatomy. The low flow impedance of the internal support structure 1021b is expected to allow flow rates of approximately 0.1 to 5 liters per minute, suitable for adequately cooling the adjacent tissue. In addition, the three-dimensional nature of the fibrous, porous structure can facilitate a uniform distribution of the heat transfer fluid 155 within the applicator 1020, producing a more uniform treatment of the adjacent tissue 110.

The porosity of the internal support structure 1021b can vary from one portion of the applicator 1020 to another, and/or can vary depending upon the local flow direction desired for the heat transfer fluid 155. For example, the porosity of the internal support structure 1021b can be selected to enhance heat transfer from the tissue in the peripheral areas of the applicator 1020, e.g., to account for the expected increase in heat transfer losses to the ambient environment in these areas. The porosity can be altered by adjusting the number and/or size of the pores within the internal support structure 1021b, as well as the spatial orientation of the pores.

From the foregoing, it will be appreciated that specific embodiments of the technology have been described herein for purposes of illustration, but that various modifications can be made without deviating from the technology. For example, the devices described above can include components that provide mechanical energy to create a vibratory, massage and/or pulsatile effect in addition to cooling the subcutaneous tissue. Representative components are described in U.S. Pat. No. 7,367,341 and in commonly assigned U.S. Patent Publication No. 2008/0287839, both of which are incorporated herein by reference. While certain features of the devices described above make them particularly suitable for home use, such features do not preclude the devices from being used in hospital or clinical office settings. In such embodiments, the devices or portions of the devices can be cooled in commercial, clinical or institutional freezers and/or coolers. The shapes, sizes and compositions of many of the components described above can be different than those disclosed above so long as they provide the same or generally similar functionalities. For example, the conduits and tubing described above can have other shapes or arrangements that nevertheless effectively convey fluid. The fluid driver can be operatively coupled to the heat transfer conduit without being directly connected to the heat transfer conduit, e.g., by being connected to the heat exchanger that conveys the heat transfer fluid, or by being connected to the applicator. The controller can implement control schemes other than those specifically described above, and/or can be coupled to sensors other than those specifically described above (e.g., pressure sensors) in addition to or in lieu of temperature and time sensors, to detect changes associated with the cooling device. The controller can in some cases accept user inputs, though in most cases, the controller can operate autonomously to simplify the use of the device. As discussed above, the coolant in some embodiments can go through a phase change during heating and cooling, so that the cooling process freezes or solidifies the coolant. In other embodiments for which no phase change occurs, the cooling process does not freeze or solidify the coolant.

Certain aspects of the technology described in the context of particular embodiments may be combined or eliminated in other embodiments. For example, the applicators described above in the content of FIGS. 9-11 can be used with any of the devices described above with reference to FIGS. 1-8. The thermal connections between the heat exchanger tubing and the coolant vessel described in the content of FIG. 8 can be applied to the arrangement shown and described in the content of FIGS. 1-3. The heaters and flow agitators described in the context of certain embodiments can be eliminated in other embodiments. Further, while advantages associated with certain embodiments of the technology have been described within the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein.

We claim:

1. A cooling device for cooling subcutaneous lipid-rich cells in a human, comprising:
    an applicator releasably positionable in thermal communication with human skin;
    an agitator;
    a coolant vessel having a coolant with a first liquid/solid phase transition temperature less than about −3° C. and greater than about −20° C., wherein a solid portion of the coolant is capable of transitioning from a solid phase to a liquid/gel phase and the agitator is capable of actuating to agitate the coolant in the liquid/gel phase in the vessel to provide a generally constant temperature environment within the coolant vessel for a treatment period;
    a heat transfer conduit operatively coupled to the applicator and housing a heat transfer fluid having a second liquid/solid phase transition temperature less than the first, the heat transfer fluid being isolated from fluid contact with the coolant;
    a heat exchanger positioned within the coolant vessel and operatively coupled to the heat transfer conduit to transfer heat between the heat transfer fluid and the coolant, the heat exchanger including a heat exchanger conduit that, together with the heat transfer conduit and the applicator, form a sealed, closed-loop path for the heat transfer fluid; and
    a fluid driver operatively coupled to the heat transfer conduit to direct the heat transfer fluid between the applicator and the heat exchanger;
    a controller in communication with the fluid driver and including a computer readable medium containing instructions that, when executed, cause the fluid driver to circulate the heat transfer fluid along the closed-loop path while the constant temperature environment within the coolant vessel is at or below 0° C. for the treatment period such that
    a surface of the applicator is at a temperature sufficiently low to disrupt the subcutaneous lipid-rich cells via thermal communication between the applicator and human skin, and
    the surface of the applicator is at the temperature for a sufficient length of time to reduce the subcutaneous lipid-rich cells via the thermal communication between the applicator and the human skin.

2. The device of claim 1 wherein the fluid driver includes a pump.

3. The device of claim 2 wherein the fluid driver further includes a pump motor, and wherein the pump motor is removable from the pump without breaking the sealed, closed loop path.

4. The device of claim 1, further comprising a heater positioned in thermal communication with the heat transfer fluid to heat the heat transfer fluid.

5. The device of claim 1 wherein the heat transfer conduit includes a supply portion positioned to deliver the heat transfer fluid to the applicator, and a return portion positioned to receive the heat transfer fluid from the applicator, and wherein the device further comprises:
    a heater positioned in thermal communication with the heat transfer conduit;

a shunt channel coupled between the supply portion and the return portion of the heat transfer conduit, in parallel with the heat exchanger;
at least one valve positioned to regulate flow through the shunt channel;
at least one sensor; and
wherein the controller is operatively coupled to the at least one sensor, the heater, the fluid driver, and the at least one valve, and wherein the computer readable medium contains additional instructions that, when executed:
 direct the at least one valve to open the shunt channel to divert heat transfer fluid around the heat exchanger;
 activate the fluid driver to pump the heat transfer fluid into the applicator;
 activate the heater; and
 deactivate the heater and direct the at least one valve to close the shunt channel based on at least one temperature signal from the at least one sensor corresponding to active heating of the heat transfer fluid.

6. The device of claim 5, further comprising a timer.

7. The device of claim 5 wherein the sensor includes a temperature sensor.

8. The device of claim 1 wherein the heat transfer conduit includes a supply portion and a return portion, the device further comprising:
 a shunt channel coupled between the supply portion and the return portion of the heat transfer conduit, in parallel with the heat exchanger; and
 at least one valve positioned to regulate flow through the shunt channel.

9. The device of claim 1 wherein the first phase transition temperature is greater than about −6° C.

10. The device of claim 1, wherein the agitator is operatively coupled to and positioned within the coolant vessel.

11. The device of claim 1 wherein the coolant is selected to include at least one of water, propylene glycol, ethylene glycol, glycerin, ethanol, isopropyl alcohol, hydroxyethyl cellulose and salt.

12. The device of claim 1 wherein the heat transfer fluid is selected to include at least one of water, propylene glycol, ethylene glycol, glycerin, ethanol, isopropyl alcohol, hydroxyethyl cellulose and salt.

13. The cooling device of claim 1 wherein the controller is programmed to cause the cooling device to circulate the heat transfer fluid such that the surface of the applicator is at the temperature for disrupting the lipid-rich cells for a time period between about 15 minutes and 2 hours.

14. A cooling device for cooling subcutaneous lipid-rich cells in a human, comprising:
 a coolant vessel having a coolant with a first liquid/solid phase transition temperature less than about −3° C.;
 a heat exchanger positioned within the coolant vessel and housing a heat transfer fluid having a second liquid/solid phase transition temperature less than the first liquid/solid phase transition temperature; and
 an applicator operatively coupled to the heat exchanger via a closed-loop path that circulates the heat transfer fluid to transfer heat from the applicator to the coolant, wherein the first liquid/solid phase transition temperature is selected to produce a temperature at the applicator that selectively reduces the lipid-rich cells via thermal communication between the applicator and human skin, and wherein the temperature produced at the applicator is less than about 0° C.;
 a fluid driver configured to be activated to direct the heat transfer fluid between the applicator and the heat exchanger; and
 a controller programmed to cause the fluid driver to circulate the heat transfer fluid along the closed-loop path while the coolant is capable of undergoing a solid to liquid/gel phase change such that the temperature of the applicator is sufficiently low for a sufficient length of time so as to reduce the lipid-rich cells via the thermal communication between the applicator and the lipid-rich cells, and wherein the controller is programmed to automatically deactivate the fluid driver based on a temperature of the coolant exceeding a threshold temperature.

15. The cooling device of claim 14, wherein the first liquid/solid phase transition temperature greater than about −20° C.

16. The cooling device of claim 14 wherein the controller is programmed to cause the fluid driver to circulate the heat transfer fluid such that the temperature of the applicator is at or below a temperature for disrupting the lipid-rich cells for a time period between about 1 minute and 2 hours.

17. The cooling device of claim 14, further comprising a heater in thermal communication with the heat transfer fluid, and wherein the controller is programmed to automatically cause the heater to increase a temperature of the heat transfer fluid when the temperature of the heat transfer fluid is lower than a predetermined temperature.

18. A cooling device for cooling subcutaneous lipid-rich cells in a human, comprising: a coolant vessel having a coolant with a first liquid/solid phase transition temperature less than about −3 degrees Celsius; a heat exchanger positioned within the coolant vessel and housing a heat transfer fluid having a second liquid/solid phase transition temperature that is less than the first liquid/solid phase transition temperature; an applicator operatively coupled to the heat exchanger via a closed-loop path that circulates the heat transfer fluid to transfer heat from the applicator to the coolant; a heater in thermal communication with the heat transfer fluid; a fluid driver configured to direct the heat transfer fluid between the applicator and the heat exchanger; and a controller programmed to automatically cause the heater to increase a temperature of the heat transfer fluid when the temperature of the heat transfer fluid is lower than a predetermined temperature, wherein the controller is programmed to automatically control activation of the fluid driver based on a temperature of the coolant, and wherein the controller is programmed to command the fluid driver to cause the heat transfer fluid to flow along the closed-loop path such that a surface of the applicator is at a sufficiently low temperature for a sufficient length of time to reduce the lipid-rich cells via thermal communication between the surface of the applicator and human skin.

19. The cooling device of claim 18 wherein the first liquid/solid phase transition temperature is lower than a temperature at which the subcutaneous lipid-rich cells are reduced such that the coolant vessel provides a substantially constant temperature environment for the heat transfer fluid while the temperature produced at the applicator is less than about 0° C.

20. The cooling device of claim 18 wherein the controller is programmed to cause the cooling device to circulate the heat transfer fluid such that the surface of the applicator is at a temperature for disrupting the lipid-rich cells for a time period between about 1 minute and 2 hours.

* * * * *